(12) United States Patent
Huang et al.

(10) Patent No.: US 8,215,834 B2
(45) Date of Patent: Jul. 10, 2012

(54) OPTICAL FIBER BASED POLYMER CORE SENSOR

(75) Inventors: Haiying Huang, Arlington, TX (US); Ayan Majumdar, San Jose, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 497 days.

(21) Appl. No.: 12/554,908

(22) Filed: Sep. 5, 2009

(65) Prior Publication Data

US 2010/0111136 A1    May 6, 2010

Related U.S. Application Data

(60) Provisional application No. 61/094,467, filed on Sep. 5, 2008.

(51) Int. Cl.
*G01K 11/00* (2006.01)

(52) U.S. Cl. ...................... 374/161; 374/159; 358/901.1

(58) Field of Classification Search .................. 374/161, 374/159; 358/901.1
See application file for complete search history.

(56) References Cited

U.S. PATENT DOCUMENTS

| | | | |
|---|---|---|---|
| 5,028,395 A * | 7/1991 | Sebille et al. | 422/82.06 |
| 5,277,872 A | 1/1994 | Bankert et al. | |
| 5,747,348 A * | 5/1998 | Jaduszliwer et al. | 436/106 |
| 7,343,060 B2 * | 3/2008 | Ohtsu et al. | 385/14 |
| 2003/0112443 A1 | 6/2003 | Hjelme et al. | |
| 2009/0074349 A1 * | 3/2009 | Hjelme et al. | 385/12 |
| 2010/0111136 A1 * | 5/2010 | Huang et al. | 374/161 |

FOREIGN PATENT DOCUMENTS

WO   WO 2010028319 A2 *   3/2010

OTHER PUBLICATIONS

Allsop, T., et al., "A High Sensitivity Refractometer Based upon a Long Period Grating Mach-Zehnder Interferometer," Review of Scientific Instruments 73:1702-1705 (2002).
Black, R.J., et al., "Tapered Single-Mode Fibres and Devices. Part 2: Experimental and Theoretical Quantification," IEEE Proc. J. 138:355-364 (1991).
Cassidy, D. T., et al., "Wavelength-Dependent Transmission of Monomode Optical Fiber Tapers", Applied Optics, 24:945-950 (1985).
Chen, X., et al., "Novel Fabry-Perot Fiber Optic Sensor with Multiple Applications", Proceedings of SPIE , vol. 5590, 2004, pp. 111-121.

(Continued)

*Primary Examiner* — Lisa Caputo
*Assistant Examiner* — Jamel Williams
(74) *Attorney, Agent, or Firm* — Daniel J. Chalker; Edwin S. Flores; Chalker Flores, LLP

(57) ABSTRACT

An optical fiber based polymer core sensor includes an optical fiber having a core and an end having a cured polymer core affixed to the core of the optical fiber. The cured polymer core extends outward from the end of the optical fiber and has a diameter approximately equal to the core of the optical fiber. Note the cured polymer core can be substantially cylindrical, tapered or geometrically shaped. The optical fiber based polymer core sensor can be used to measure a temperature, measure a strain, measure a distance, measure a refractive index, detect or measure an analyte, detect a toxin, detect a biological agent, monitor a chemical process, or a combination thereof.

26 Claims, 14 Drawing Sheets

OTHER PUBLICATIONS

Cox, F. M., et al., "Opening up Optical Fibres", Opt. Exp., 15:11843-18848 (2007).

Culshaw, B., et al., "Evanescent Wave Methane Detection Using Optical Fibers", Electron. Lett. 28:2232-2234 (1992).

Ding, J., et al., "Fiber-Taper Seeded Long-Period Grating Pair as a Highly Sensitive Refractive-Index Sensor", IEEE Phot. Tech. Lett. 17:1247-1249 (2005).

Frisken, S.J., "Light-Induced Optical Waveguide Uptapers", Opt. Lett. 18, 1035-1037 (1993).

Hocine, M., et al., "Modeling the Growth of a Polymer Microtip on an Optical Fiber End", J. Opt. Soc. Am. B 23:611-620 (2006).

Huang, Z., et al., "Intrinsic Fabry-Perot Fiber Sensor for Temperature and Strain Measurements", IEEE Phot. Tech. Lett. 17:2403-2405 (2005).

Iadicicco, A., et al., "Thinned Fiber Bragg Gratings as Refractive Index Sensors", IEEE Sens. J., 5:1288-1295 (2005).

Iadicicco, A., et al., "Refractive Index Sensor Based on Microstructured Fiber Bragg Grating", IEEE Phot. Tech. Lett., 17:1250-1252 (2005).

Kim, D.W., et al., "Simultaneous Measurement of Refractive Index and Temperature Based on a Reflection-Mode Long-Period Grating and an Intrinsic Fabry—Perot Interferometer Sensor", Optics Letters, vol. 30, 2005, pp. 3000-3002.

Lacroix, S., et al., "Tapered Monomode Optical Fibers: Understanding Large Power Transfer", Applied Optics 25:4421-4425 (1986).

Lee, C.E., et al., "Optical Fiber Fabry-Perot Embedded Sensor", Optics Letters, vol. 14, 1989, pp. 1225-1227.

Majumdar, A., Huang, H., "Development of an In-Fiber Whitelight Interferometric Distance Sensor for Absolute Measurement of Arbitrary Small Distances", Applied Optics, 47:2821-2828 (2008).

Newby, K., et al., "Remote Spectroscopic Sensing of Chemical Absorption Using a Single Multimode Optical Fiber", App. Opt., 23:1812-1815 (1984.).

Patrick, H. J., et al., "Analysis of the response of long period fiber gratings to external index of refraction", J. Lightwave Tech., 16:1606-1612 (1998).

Phan, M. C., et al., "Fibre Bragg grating photowriting in microstructured optical fibers for refractive index measurement", Measurement Science & Technology 17:992-997 (2006).

Schroeder, K., et al., "A Fiber Bragg Grating Refractometer", Meas. Sci. Technol., 12:757-764 (2001).

Schwider, J., et al., "Dispersive Interferometric Profilometer", Optics Letters, vol. 19, 1994, pp. 995-997.

Singh, H., Sirkis, J. S., "Simultaneously Measuring Temperature and Strain Using Optical Fiber Microcavities", Journal of Lightwave Technology, 15:647-653 (1997).

Snyder, A. W., "Coupling of Modes on a Tapered Dielectric Cylinder", IEEE Transactions on Microwave Theory and Techniques 18:383-392 (1970).

Sugihara, O., et al., "Light-Induced Self-Written Polymeric Optical Waveguides for Single-Mode Propagation and for Optical Interconnections", IEEE Phot. Tech. Lett. 16:804-806 (2004).

Tian, Z., et al., "Refractive Index Sensor Based on Abrupt Taper Michelson Interferometer in a Single-Mode Fiber", Opt. Lett., 33:1105-1107 (2008).

Tsai, W. H., Lin, C. J., "Novel Structure for the Intrinsic Fabry-Perot Fiber Optic Temperature Sensor", Journal of Lightwave Technology, 19:682-686 (2001).

Zhang, Z., et al., "Thermo-Optic Coefficients of Polymers for Optical Waveguide Applications", Polymer, 47:4983-4986 (2006).

International Search Report and Written Opinion for PCT/US2009/056142 dated Apr. 16, 2010.

Huang, H., et al., "An Inexpensive Technique to Fabricate Hybrid Glass/Plastic Optical Fiber Sensors for Structural Health Monitoring," 4th Intermediate Conference on Earthquake Engineering, Oct. 2006, No. 293.

Zhang, Z., et al., "Thermo-optic coefficients of polymers for optical waveguide applications," Polymer (2006), 47:4893-4896.

* cited by examiner

OPTICAL FIBER BASED POLYMER CORE SENSOR

CROSS-REFERENCE TO RELATED APPLICATIONS

This application claims benefit of U.S. Provisional application Ser. No. 61/094,467 filed on Sep. 5, 2008, which is incorporated herein by reference in its entirety.

STATEMENT OF FEDERALLY FUNDED RESEARCH

This invention was made with U.S. Government support under Contract No. CMS-0650716 awarded by the NSF. The government has certain rights in this invention.

FIELD OF THE INVENTION

The present invention relates generally to the field of optical fiber sensors and, more particularly, to an optical fiber based polymer core sensor.

BACKGROUND OF THE INVENTION

Without limiting the scope of the invention, its background is described in connection with optical fiber sensors and their applications.

Most optical fiber biochemical sensors are based on measuring the RI of bio/chemical liquids using various sensing schemes such as interferometry [1], fiber gratings [2-5], and specialty fibers [7-11]. Interferometer-based RI sensors usually consist of two arms of light; one arm of light is influenced by the external medium and thus serves as the sensing arm while the other arm of light is used as the reference. When these two arms are combined to generate an interference pattern, a change in the external RI alters the optical path length of the sensing arm and thus causes a shift in the interference pattern. Interferometric RI sensors often require a mechanism to split the incoming light into two arms, resulting in a more complicated sensor system. Two types of fiber gratings, i.e. Fiber Bragg Grating (FBG) and Long Period Fiber Grating (LPFG), are commonly exploited for RI measurement. RI changes are measured from the shifts of the transmission/reflectance spectra due to the influence of the external RI on the coupling conditions of the fiber gratings. Because an LPFG couples the light from the core mode to the cladding modes, its transmission spectrum is highly sensitive to the changes of the external RI [2]. In comparison, the FBG-based RI sensors are usually much less sensitive because the light is mainly confined within the fiber core region. In order to increase the sensitivity, the cladding surrounding a FBG is often etched or thinned [3-4]. RI sensors based on fiber grating are usually expensive because of the stringent grating fabrication processes. Specialty fibers such as tapered fiber [7-8], and D-shaped fiber [9], microstructured fiber [10], and cladding stripped fiber [11] have also been developed for biochemical sensing. These types of optical fiber biochemical sensors require accessing the evanescent field at the fiber core/cladding interface. As such, precision micromachining is required in order to remove a part of the fiber cladding. In addition, many of these RI sensors require a long interaction length of more than a few millimeters to achieve a high RI sensitivity better than or comparable to the reported RI sensors [1,3,5-8].

For example, United States Published Patent Application No. 20030112443 (Hjelme et al.) describes a chemical sensing probe that detects chemical contents based on the volume change or the refractive index change of the chemically sensitive sensing materials that fill a Fabry-Perot cavity. The sensor requires the chemically sensitive sensing materials to react with the chemical contents so that either its volume or refractive index is changed. The change in volume and/or refractive index gives a change in an optical path length through the probe which can be measured interferometrically.

United States Published Patent Application No. 20090074349 (Hjelme et al.) describes the fabrication of interferometric fiber optic probes employing hydrogel sensor material that is responsive to an analyte; and to probes produced thereby. The invention relates particularly to probes which are suitable for invasive measurements of analytes in a live body. The sensor is fabricated on one fiber while the UV light is delivered by a second fiber.

U.S. Pat. No. 5,277,872 (Bankert) describes an optical fiber pH microsensor that includes an optical fiber having a portion of the surface of a light conducting core covered with a layer of a pH sensitive dye material. The dye material is covalently bonded to a polymeric matrix which is in turn covalently bonded to the optical fiber core to prevent leaching of the indicator dye material during extended use. The dye material is crosslinked in situ over the tip of the optical fiber core to yield a hydrophilic, ion permeable pH sensor which can be used intravascularly to monitor blood pH.

In addition, optical fiber sensors have also been widely used for temperature sensing since they have many advantages than conventional temperature sensors, e.g., they can safely operate in strong electromagnetic fields, in explosive or chemically aggressive environment and at areas under high voltage [12]. Among various fiber optic sensors, Fabry-Perot interferometric (FPI) sensors have distinct advantages over the others such as compactness, high sensitivity, small size, and polarization independence. FPI-based fiber optic sensors can be grouped as extrinsic FPI (EFPI) sensors and intrinsic FPI (IFPI) sensors. For EFPI sensors, the light signal is delivered and collected by the optical fiber and the modulation of the light occurs outside of the fiber. While in the IFPI sensor, the modulation of the light takes place inside the fiber. As "all fiber" sensors, IFPI sensors can reduce or eliminate the bonding problems experienced with extrinsic sensors. IFPI sensors are also more versatile for installation and are more robust. On the other hand, IFPI sensors are usually more difficult and expensive to fabricate [13]. Most of the reported IFPI sensors are based on manufacturing thin-film mirrors on the cleaved fiber end-face through vacuum deposition, magnetron sputtering or electron-beam evaporation [14-15]. However, thin film mirrors can easily be damaged. Besides, it is difficult to control the film thickness and flatness with precision. Another method that is being used to manufacture IFPI sensors is splicing two fibers with different core diameters as a reflective mirror [16]. But in order to fabricate an IFPI sensor with this configuration, the ends of fibers have to be polished with four different polishing films beforehand to prevent large power losses, which is a long and tedious process [16].

There is, therefore, a need for an optical fiber sensor that provides improved sensitivity and does not require specialized or complex materials.

SUMMARY OF THE INVENTION

The fabrication, analysis, and evaluation of a compact refractive index (RI) and temperature sensor using a micro-sized polymer core fabricated at the end of an optical fiber that uses low-cost commercial products and simplified fabrication techniques is described herein. The refractive index of the polymer used is different from that of the optical fiber so that a part of the light traveling in the optical fiber can be reflected at the fiber/polymer interface. The polymer tip serves as a Fabry-Perot interferometric cavity so that a phase shift is introduced to the light propagating in it when the RI of the surrounding medium changes and thus causes a fringe shift in the interferometric fringe spectrum. With respect to temperature measurements, the optical path traveled by the light coupled into the polymer tip changes with the ambient temperature due to the combination of thermal expansion and thermo-optic effect. Because the polymer tip has a high thermo-optic coefficient compared to silica, the temperature sensitivity of the sensor when used for temperature measurements is higher than most of the reported sensors that works under the same principle. The sensitivity of the sensor can be adjusted or modified by changing the length or shape of the polymer tip length and/or tailoring the properties of the polymer material. Moreover, the present invention does not require the use of cladding materials, dyes, etching or complex fabrication techniques. As a result, the present invention provides greater sensitivity and overcomes many of the limitations of other optical fiber based sensors.

More specifically, the present invention provides an optical fiber based polymer core sensor that includes an optical fiber having a core and an end having a cured polymer core affixed to the core of the optical fiber. The cured polymer core extends outward from the end of the optical fiber and has a diameter approximately equal to the core of the optical fiber. Note the cured polymer core can be substantially cylindrical, tapered or geometrically shaped. The optical fiber based polymer core sensor can be used to measure a temperature, measure a strain, measure a distance, measure a refractive index, detect or measure an analyte, detect a toxin, detect a biological agent, monitor a chemical process, or a combination thereof.

In addition, the present invention provides a method for fabricating an optical fiber based polymer core sensor. An optical fiber having a core is provided. A flat reflective object is aligned with the core of the optical fiber to provide a gap between the core and the flat reflective object. The flat reflective object can be a second optical fiber, a mirror or other suitable object. A light-curable polymer is deposited within the gap. A light is transmitted through the core such that the light-curable polymer forms a cured polymer core connecting the core to the reflective object. The cured polymer core has a diameter approximately equal to the core. The reflective object is then removed such that the cured polymer core remains affixed to the optical fiber.

Moreover, the present invention provides a method for fabricating an optical fiber based polymer core sensor. An optical fiber having a core is provided. A flat reflective object is aligned with the core of the optical fiber to provide a gap between the core and the flat reflective object. The flat reflective object can be a second optical fiber, a mirror or other suitable object. A white light is transmitted through the optical fiber. The gap is measured using the optical fiber and the reflective object as a white light Fabry-Perot interferometric distance sensor. The gap is adjusted to provide a specified distance between the optical fiber and the reflective object. A light-curable polymer is deposited within the gap. A light is transmitted through the core such that the light-curable polymer forms a cured polymer core connecting the core to the reflective object. The reflective object is then removed such that the cured polymer core remains affixed to the optical fiber. Any uncured light-curable polymer is removed. The cured polymer core and a portion of the optical fiber are then packaged.

The present invention is described in detail below with reference to the accompanying drawings.

BRIEF DESCRIPTION OF THE DRAWINGS

The above and further advantages of the invention may be better understood by referring to the following description in conjunction with the accompanying drawings, in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. The discussion herein relates primarily to optical fiber based polymer core sensors for refractive index and temperature sensor, but it will be understood that the concepts of the present invention are applicable to any optical fiber based sensors for strain measurement, distance measurement, toxin detection, biological agent detection, chemical process monitoring, pH measurement, analyte measurement, etc.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The fabrication, analysis, and evaluation of a compact refractive index (RI) and temperature sensor using a micro-sized polymer core fabricated at the end of an optical fiber that uses low-cost commercial products and simplified fabrication techniques is described herein. The refractive index of the polymer used is different from that of the optical fiber so that a part of the light traveling in the optical fiber can be reflected at the fiber/polymer interface. The polymer tip serves as a Fabry-Perot interferometric cavity so that a phase shift is introduced to the light propagating in it when the RI of the surrounding medium changes and thus causes a fringe shift in the interferometric fringe spectrum. With respect to temperature measurements, the optical path traveled by the light coupled into the polymer tip changes with the ambient temperature due to the combination of thermal expansion and thermo-optic effect. Because the polymer tip has a high thermo-optic coefficient compared to silica, the temperature sensitivity of the sensor when used for temperature measurements is higher than most of the reported sensors that works under the same principle. The sensitivity of the sensor can be adjusted or modified by changing the length or shape of the polymer tip length and/or tailoring the properties of the polymer material. Moreover, the present invention does not require the use of cladding materials, dyes, etching or complex fabrication techniques. As a result, the present invention overcomes many of the limitations of other optical fiber based sensors.

Figure 1:
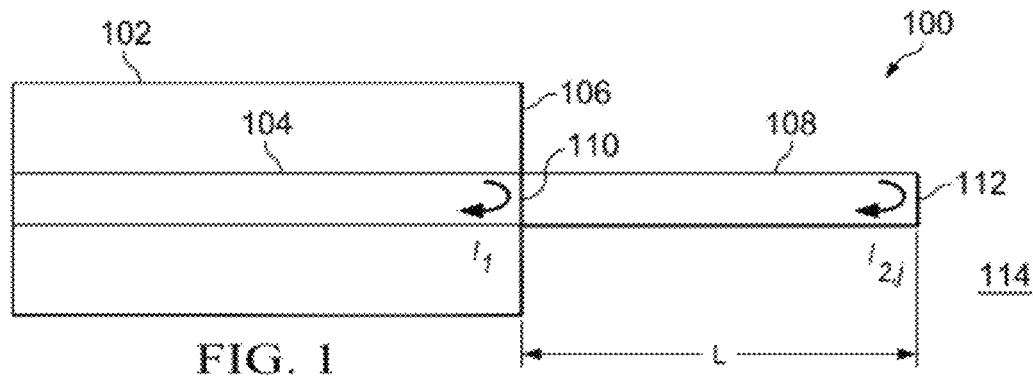
FIG. 1 is a diagram of an optical fiber based polymer core sensor in accordance with one embodiment of the present invention.

Now referring to FIG. 1, a diagram of an optical fiber based polymer core sensor 100 in accordance with one embodiment of the present invention is shown. An optical fiber 102 having a core 104 and an end 106, such as a single-mode optical fiber (SMF), has a cured polymer core 108 affixed to and aligned with the core 104 of the optical fiber 102. The cured polymer core 108 extends outward from the end 106 of the optical fiber 102, and has a length L and a diameter approximately equal to the core 104 of the optical fiber 102. Note the cured polymer core 108 can be substantially cylindrical, tapered or geometrically shaped. Moreover, the light-curable polymer used to fabricate the cured polymer core 108 can be selected or modified to adjust a sensitivity or a range of the sensor 100. The optical fiber based polymer core sensor 100 can be used to measure a temperature, measure a strain, measure a distance, measure a refractive index, detect or measure an analyte, detect a toxin, detect a biological agent, monitor a chemical process (e.g., chemical plants, energy industry, air bubbles in concrete, resin curing, etc.), or a combination thereof.

When light traveling inside the optical fiber 102 encounters the fiber/polymer interface 110, a portion of the light $I_1$ is reflected due to the difference in RIs of the optical fiber 102 and the cured polymer core 108. The light transmitted into the polymer core 108 propagates along the polymer core 108 and are again partially reflected $I_{2,j}$ at the end 112 of the polymer core 108 due to the RI difference between the polymer core 108 and the surrounding medium 114. Tracing its path back, this reflected light $I_{2,j}$ reenters the optical fiber 102 and interferes with the light reflected at the SMF/polymer interface 110. As a result, the polymer core 108 serves as a Fabry-Perot interference (FPI) cavity, encoding the reflectance spectrum of the optical fiber sensor 100 with interference fringes. A change in the RI of the surrounding medium 114 alters the propagation constant of the light propagating inside the polymer core 108 and thus causes a shift of the fringe spectrum. By detecting the fringe shift using an optical spectrum analyzer, the correlation between the fringe shift and the RI change can be established. Note that depending on the intended use of the sensor 100, the polymer core 108 and a portion of the optical fiber 102 will typically be disposed within a package (not shown).

Figure 2:
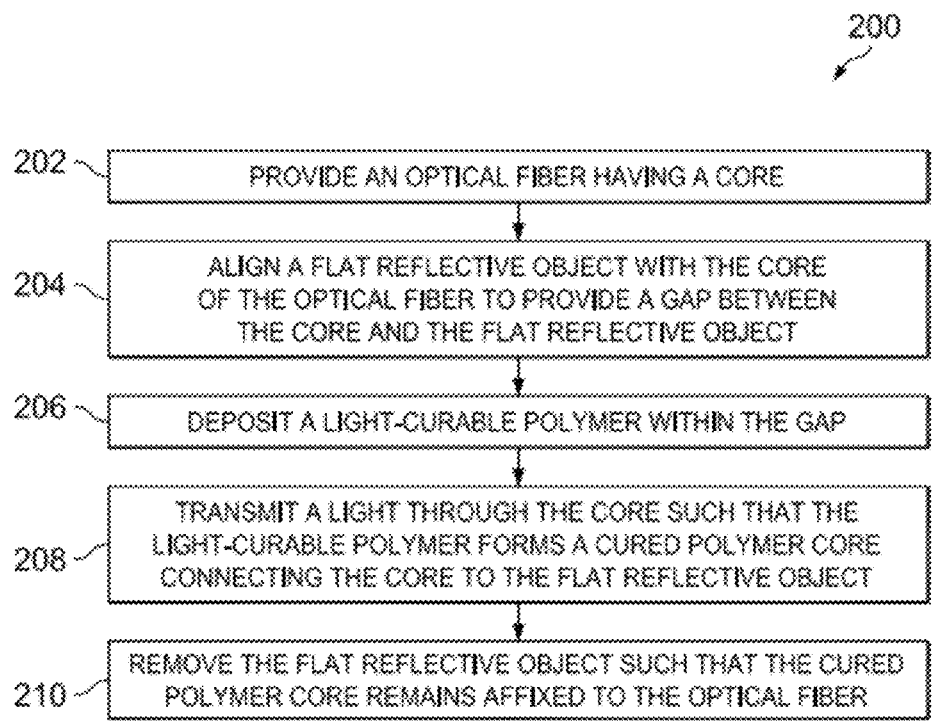
FIG. 2 is a flow chart illustrating a method of fabricating an optical fiber based polymer core sensor in accordance with one embodiment of the present invention.

Referring now to FIG. 2, a flow chart illustrating a method 200 for fabricating an optical fiber based polymer core sensor 100 in accordance with one embodiment of the present invention is shown. An optical fiber 102 having a core 104 is provided in block 202. A flat reflective object is aligned with the core 104 of the optical fiber 102 to provide a gap L between the core 104 and the flat reflective object in block 204. The flat reflective object can be a second optical fiber, a mirror or other suitable object. A light-curable polymer is deposited within the gap L in block 206. The light-curable polymer can be a UV-curable polymer, such as a UV-curable optical epoxy. The light-curable polymer is selected or modified to adjust a sensitivity or a range of the refractive index sensor. A light is transmitted through the core 104 such that the light-curable polymer forms a cured polymer core 108 connecting the core 104 to the reflective object in block 208. The light is generated using a light-emitting-diode (LED) or other light source attached to the optical fiber 102 that is suitable for curing the light-curable polymer. The cured polymer core 108 has a diameter approximately equal to the core 104. The reflective object is then removed in block 210 such that the cured polymer core 108 remains affixed to the optical fiber 102.

Figure 3:
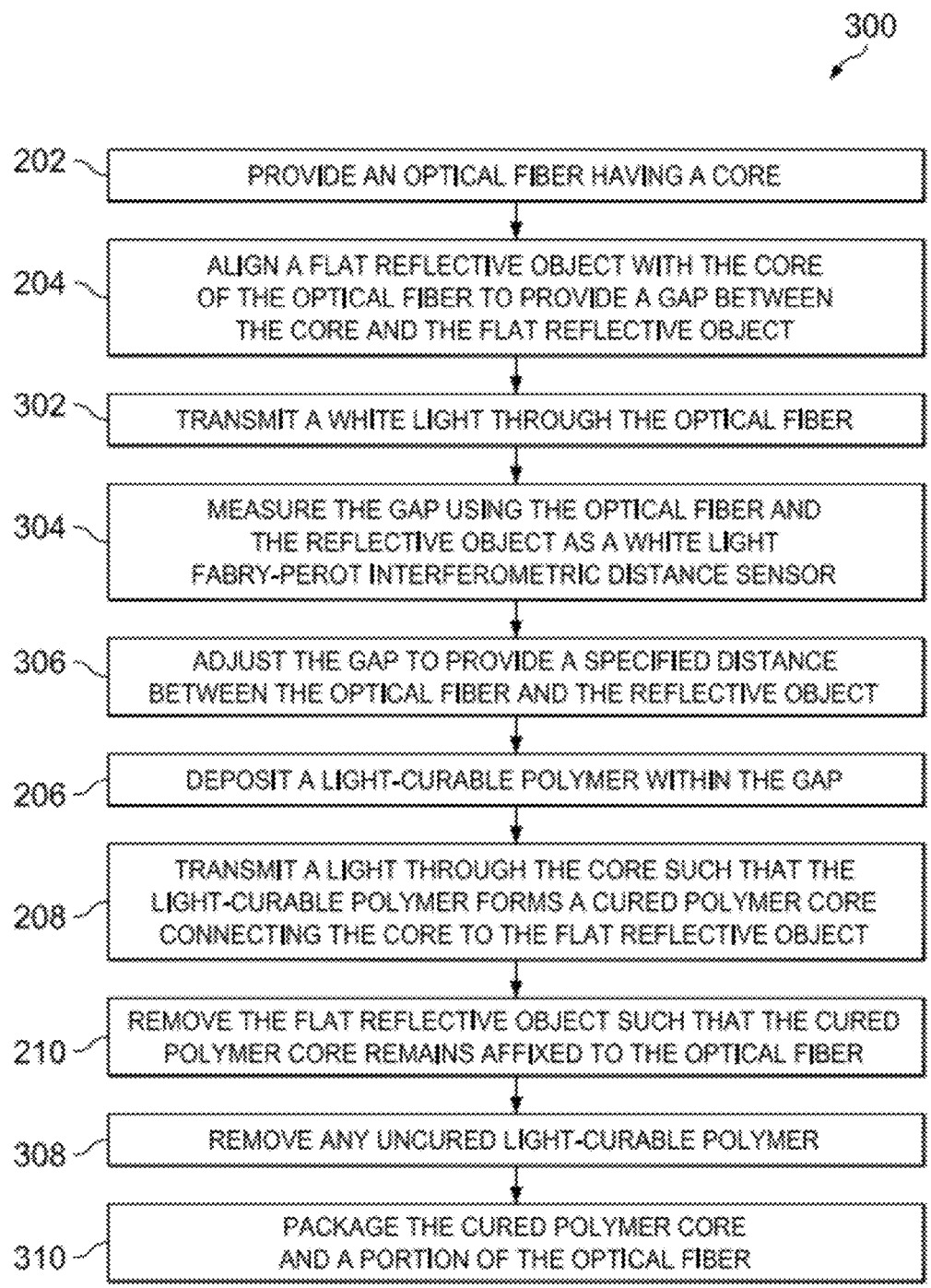
FIG. 3 is a flow chart illustrating a method of fabricating an optical fiber based polymer core sensor in accordance with another embodiment of the present invention.

Now referring to FIG. 3, a flow chart illustrating a method 300 for fabricating an optical fiber based polymer core sensor 100 in accordance with another embodiment of the present invention is shown. An optical fiber 102 having a core 104 is provided in block 202. A flat reflective object is aligned with the core 104 of the optical fiber 102 to provide a gap L between the core 104 and the flat reflective object in block 204. The flat reflective object can be a second optical fiber, a mirror or other suitable object. A white light is transmitted through the optical fiber 102 in block 302. The gap is measured in block 304 using the optical fiber and the reflective object as a white light Fabry-Perot interferometric distance sensor. The gap is adjusted in block 306 to provide a specified distance between the optical fiber and the reflective object. A light-curable polymer is deposited within the gap L in block 206. The light-curable polymer can be a UV-curable polymer, such as a UV-curable optical epoxy. The light-curable polymer is selected or modified to adjust a sensitivity or a range of the refractive index sensor. A light is transmitted through the core 104 such that the light-curable polymer forms a cured polymer core 108 connecting the core 104 to the reflective object in block 208. The light is generated using a light-emitting-diode (LED) or other light source attached to the optical fiber 102 that is suitable for curing the light-curable polymer. The cured polymer core 108 has a diameter approximately equal to the core 104. The reflective object is then removed in block 210 such that the cured polymer core 108 remains affixed to the optical fiber 102. Any uncured light-curable polymer is removed in block 308. Note that this step can be performed before the reflective object is removed. The cured polymer core 108 and a portion of the optical fiber are then packaged in block 210, such as being packaged within a capillary tube. Other steps may include modifying a shape of the cured polymer core wherein the modified shape of the cured polymer core is tapered or geometrically shaped. Note that a mold could be attached to the optical fiber 102 to form the cured polymer core 108 into a particular shape.

A more detailed description of a manufacturing process used to fabricate a sensor in accordance with the present invention will now be described. The polymer core is fabricated using the light-induced self-written (LISW) optical waveguide technology [23-24]. Unlike sensors previously reported in the literature and the prior art that uses a laser light and a custom-mixed resin to fabricate the waveguide, the present invention provides an economical technique that uses low-cost components, namely a UV light-emitting-diode (LED) and an UV-curable optical adhesive, to fabricate the polymer core. A UV LED (Nichia NSHU550A, wavelength 375 nm) is coupled to a single mode fiber (SMF). The cleaved SMF is mounted on a three-axis fiber alignment stage and is manually aligned with the LED. Different coupling mechanisms were studied. It was discovered that the maximum coupling from the LED to the SMF was achieved by removing the glass cover of the LED and directly butting the optical fiber against the LED chip. An optical power meter was employed to monitor the output power of the SMF during the alignment process in order to provide position feedbacks for the alignment. For a SMF of 0.5 m in length, the output power was 180 nW for a forward current of 50 mA. Even though the total output power was low, the power density of the UV light was sufficient to cure the epoxy in a few seconds.

Figure 4:
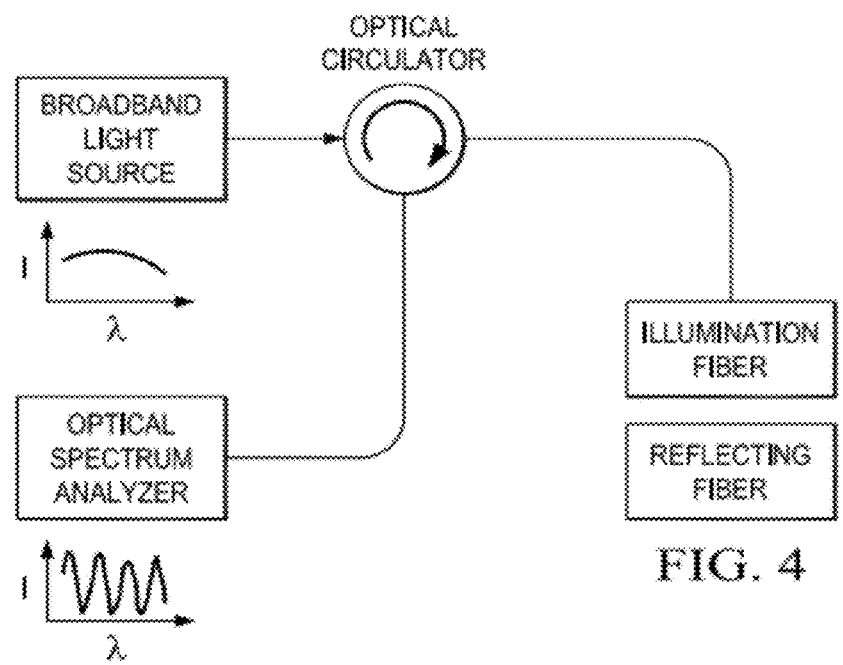
FIG. 4 is a diagram of the whitelight reflectance spectrum measurement system in accordance with the present invention.

In order to control the length of the polymer tip, two SMFs facing each other were first aligned under a microscope. The alignment mechanism consists of two V-grooved fiber holders. One is stationary while the other is mounted on a three-axis translation stage. The fiber on which the polymer tip is to be fabricated was mounted on the stationary stage. A second fiber was placed in the V-groove mounted on a translation stage so that it can be aligned to face the original fiber using the translation stage. An optical microscope was used to view the alignment at a greater magnification and help performing finer adjustments of the fiber position. The gap between the two fibers can be changed by traversing the translational stage along the fiber axis. Since the two fibers form a Fabry-Perot cavity, the gap between the two fibers can be measured by connecting the second fiber to a whitelight reflectance spectrum measurement system as shown in FIG. 4.

Figure 5:
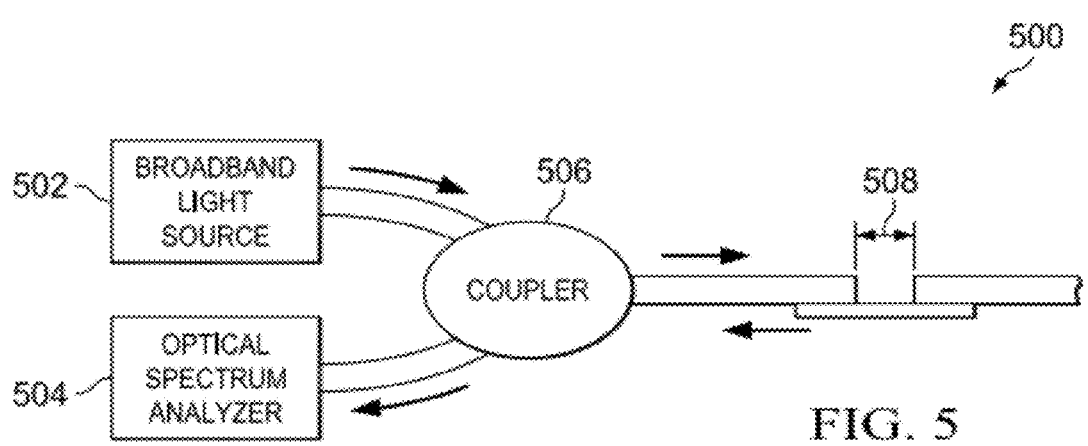
FIG. 5 shows a set up for monitoring the gap during sensor fabrication in accordance with the present invention.

The schematic for the set-up 500 used in the sensor evaluation is shown in FIG. 5. The edge-emitting light emitting diode (EELED) of an Optical Spectrum Analyzer (OSA Agilent 86142B) was used as the broadband light source 502. A 3 dB coupler 506 was employed to direct the light emitted from the light source 502 to the fiber gap 508 and to route the reflected light toward to the OSA 504. This reflected light was then received by the OSA 504 and its spectrum can be acquired. The procedure to demodulate the distance between the two fibers from the measured reflectance spectrum can be found in [25]. The data from the OSA 504 is converted to a wavenumber domain which is passed through a low pass filter. The output of the filter is normalized and processed using a Hanning window and Fast Fourier Transform (FFT).

Figure 6A:
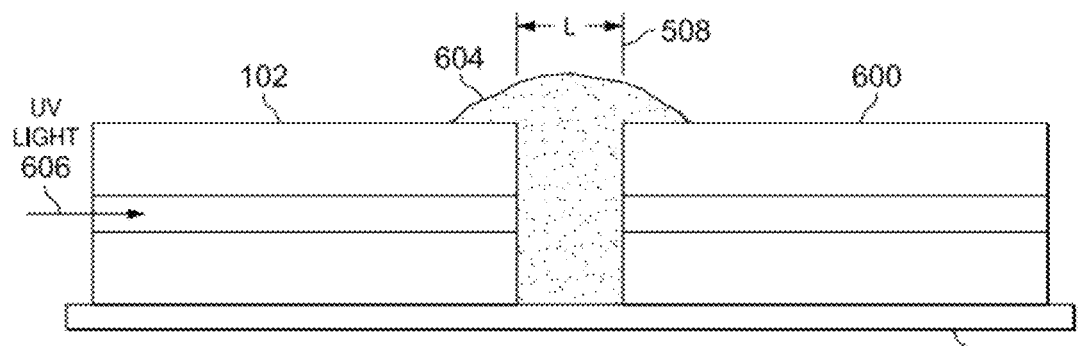
FIGS. 6A-6C show diagrams of the sensor during the fabrication process in accordance with one embodiment of the present invention.
Figure 6B:
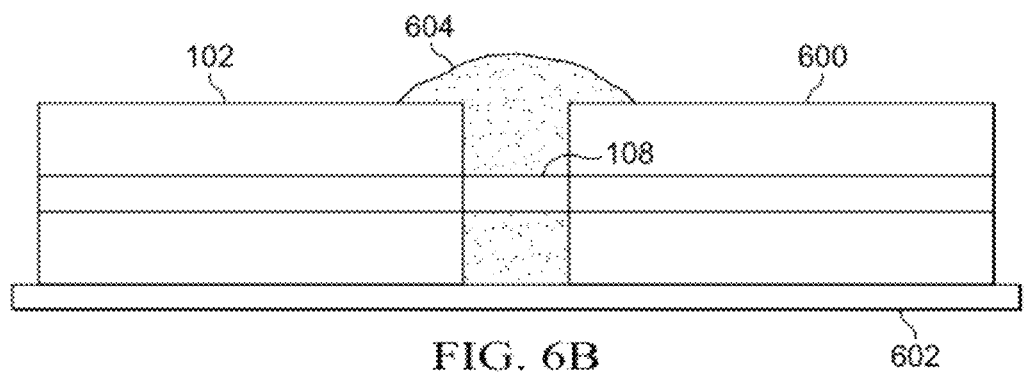
Figure 6C:
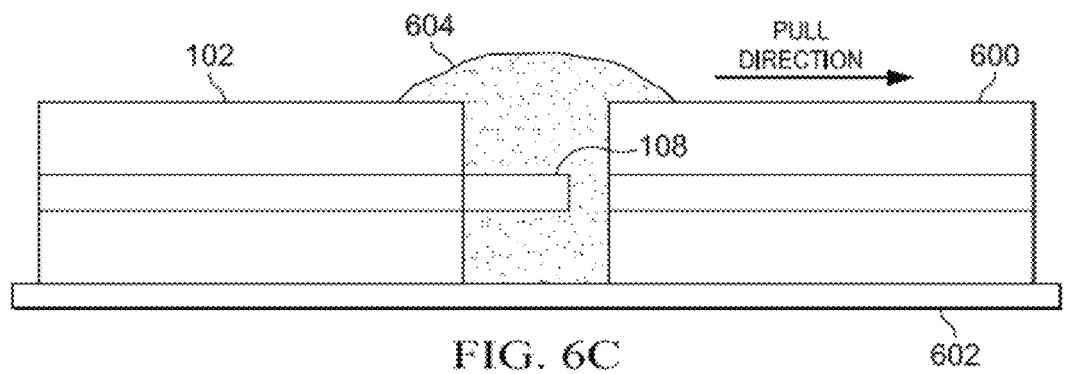
Figure 7A:
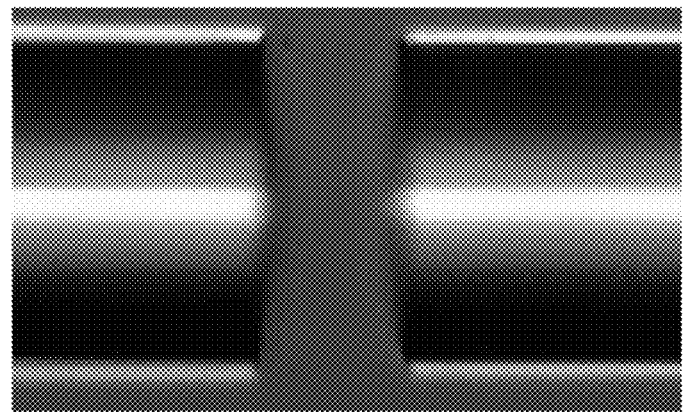
FIGS. 7A-7C show micrographic images of the sensor during fabrication stages in accordance with one embodiment of the present invention.
Figure 7B:
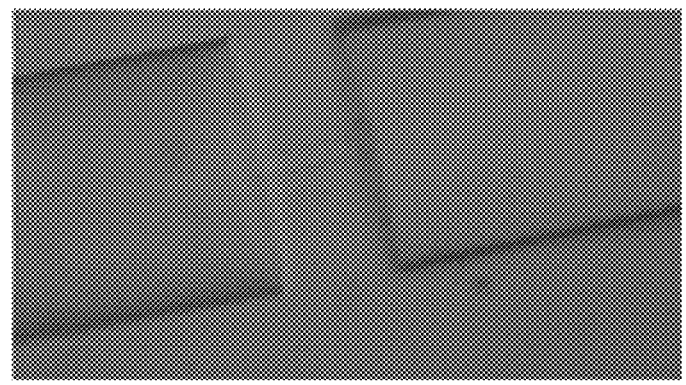
Figure 7C:
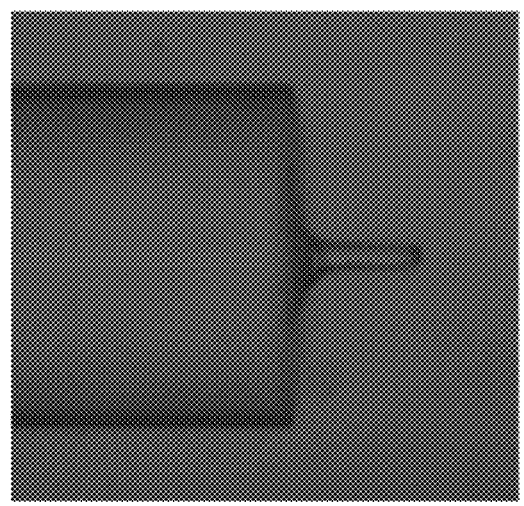

Now referring to FIG. 6A-6C, diagrams of the sensor during the fabrication process in accordance with one embodiment of the present invention are shown. As shown in FIG. 6A, after the optical fiber 102 and reflective object 600 (second optical fiber) were aligned properly, a microscope slide 602 holding a pool of UV curable epoxy 604, such as NOA61 or NOA68 (Norland Products), was slowly raised toward the two fibers 102 and 600 using a translation stage until the two fibers were submerged under the UV curable epoxy 604. The UV light 606 is coupled into the illumination fiber 102 by connecting its free end to the fiber that is coupled to the light source (UV LED). As shown in FIG. 6B, the UV light exiting the illumination fiber forms a cured polymer core 108 between the two fibers. Because the cured polymer 108 has a higher RI than the uncured polymer 604, it acts as a waveguide that confines the UV light inside the cured polymer core [26]. As such, the diameter of the cured polymer 108 core does not change with the duration of the UV exposure. The inventors were able to consistently produce polymer cores that are automatically aligned with the fiber core and have approximately the same diameter as that of the fiber core. As shown in FIG. 6C, once the polymer core 108 was formed, the second fiber 600 was slowly pulled away from the illumination fiber 102 using the translation stage. Because the polymer core 108 has a stronger bond to the illumination fiber 102 than to the second fiber 600, it breaks off from the second fiber 600 first and remains attached to the illumination fiber 102. Furthermore, the polymer core 108 returned to its original shape after the separation, due to its elastic properties. The micrographic images of the sensor fabrication stages are shown in FIGS. 7A and 7B and the image of the fabricated polymer core in alcohol is shown in FIG. 7C. The length of the polymer core 108, calculated from the reflectance spectrum of the sensor when it is surrounded by air and the RI of the cured epoxy provided by the manufacturer, is calculated to be 34.5 μm.

Figure 8:
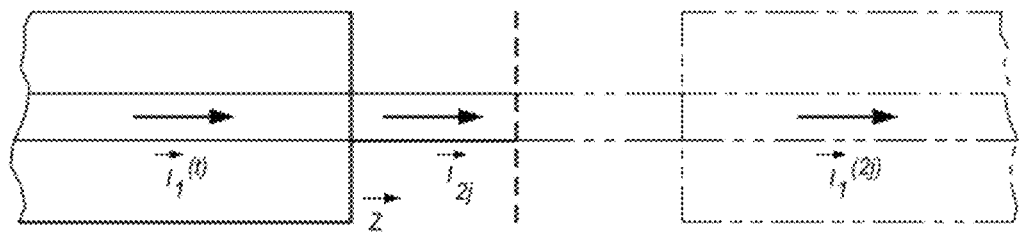
FIG. 8 shows the transfer of power of the light traveling in the polymer core in accordance with the present invention.

Referring now to FIG. 8, an analysis of the sensor for use in RI measurements in accordance with the present invention will now be described. When the polymer core is submerged into a liquid, the polymer core and the liquid form a waveguide if the RI of the liquid is smaller than that of the polymer core. Assume the RI of the liquid is 1.4~1.44, the polymer core functions as a multi-mode fiber ($n_{core}$=1.56, $n_{clad}$=1.4~1.44, V=14~12 at 1310 nm). As such, the fundamental mode $\vec{I}_1$ propagating in the SMF is coupled to higher order modes $\vec{I}_{2j}$ when it is transmitted to the polymer core. Reflecting at the end of the polymer core, these higher order modes are partially converted back to the fundamental mode when they re-enter the SMF. Denoting the fundamental mode that is coupled from the $j^{th}$ mode $\vec{I}_{2j}$ as $\vec{I}_1^{2j}$, the reflectance spectrum of the RI sensor can be calculated as:

$$I(\lambda) = \left| I_1^{(r)} + \vec{I}_1^{(2j)} \right| \qquad (1)$$
$$= \sum_j \left| I_1^{(r)} \exp(-j\phi_1) + I_1^{(2j)} \exp(-j\phi_{2j}) \right|,$$

where $I_1^{(r)}$ and $\phi_1$ represent the intensity and the phase of the fundamental mode reflected at the SMF/polymer core interface while $I_1^{(2j)}$ and $\phi_{2j}$ are the intensity and the phase of $\vec{I}_1^{2j}$. Expressing the incoming light as h $\vec{I}_1 = I_1 \exp(-j\phi)$, $I_1^{(r)}$ and $\phi_1$ are calculated as:

$$I_1^{(r)} = R_1 I_1 = \left(\frac{n_{polymer} - n_{SMF}}{n_{polymer} + n_{SMF}}\right)^2 I_1 \quad (2)$$

and $$\phi_1 = \phi + \pi,$$

where $R_1$ is the reflectivity of the SMF/polymer interface and is determined by the RIs of the polymer core $n_{polymer}$ and the SMF $n_{SMF}$ [17]. The reflection of $\vec{T}_{2j}$ at the end of the polymer core is equivalent to the transmission of $\vec{T}_{2j}$ to a mirror image of the RI sensor. The power evolution of $\vec{T}_{2j}$, therefore, is similar to the large power transfer between the fundamental mode and the higher order modes in abruptly tapered fibers [18-19]. The light transmitted to the polymer core at the SMF/polymer interface is given by $$\vec{T}_1^{(t)} = (1 - R_1) I_1 \exp(-j\phi). \quad (3)$$

Denoting the percentage of light coupled from $\vec{T}_1^{(t)}$ to $\vec{T}_{2j}$ as $C_{1j}$, $\vec{T}_{2j}$ along the length of polymer core can be expressed as:

$$\vec{T}_{2j}(z) = C_{1j} I_1^{(t)} \exp\left[-j\phi - j\int_0^z \beta_j(\zeta) d\zeta\right], \quad (4)$$

where $\beta_j(z)$ is the propagation constants of the $j^{th}$ mode inside the polymer core. The light after the reflection at the end of the polymer core is:

$$\vec{T}_{2j}(z) = R_2 C_{1j} I_j^{(t)} \exp\left[-j(\phi + \pi) - j\int_0^z \beta_j(\zeta) d\zeta\right], \quad (5)$$

where the reflectivity $R_2$ at the polymer/medium interface is calculated from the RIs of the polymer core and the surrounding medium, i.e.

$$R_2 = \left(\frac{n_{polymer} - n_m}{n_{polymer} + n_m}\right)^2.$$

A phase shift of $\pi$ is introduced because it is a reflection instead of a transmission. Finally, the light re-entering the SMF is calculated as:

$$\vec{I}_1^{(2j)} = \sum_j C_{j1}(1 - R_1)\vec{I}_{2j}(2L) \quad (6)$$

$$= \sum_j (1 - R_1)^2 R_2 C_{j1} C_{1j} I_1 \exp\left[-j(\phi + \pi) - j\int_0^{2L} \beta_j(\zeta) d\zeta\right].$$

$C_{j1}$ represents the percent of light coupled from $\vec{T}_{2j}$ to $\vec{T}_1^{(2j)}$ and L is the physical length of the polymer core. Assuming the polymer core has a uniform RI along its length, Eq. (6) can be simplified as:

$$\vec{I}_1^{(2j)} = \sum_j I_1^{(2j)} \exp[-j(\phi + \pi) - j2\beta_j L]. \quad (7)$$

Combining Eq. (1), (2) and (7), the reflectance spectrum of the RI sensor is:

$$I(\lambda) = I_1^{(r)} + \sum_j I_1^{(2j)} + \quad (8)$$

$$\sum_j \sqrt{I_1^{(r)} I_1^{(2j)}} \cos(2\beta_j L) + \sum_{i \neq j} \sqrt{I_1^{(2i)} I_1^{(2j)}} \cos[2(\beta_j - \beta_i) L].$$

A change of the external RI changes the propagation constants $\beta_j$ and thus shifts the reflectance spectrum. Based on Eq. (8), there are two effects that contribute to the phase shift. The $$\sum_j \sqrt{I_1^{(r)} I_1^{2j}} \cos(2\beta_j L)$$

term is due to the Fabry-Perot interference between $\vec{T}_1^{(r)}$ and $\vec{T}_{2j}$ while the $$\sum_{i \neq j} \sqrt{I_1^{2i} I_1^{2j}} \cos[2(\beta_j - \beta_i) L]$$

term is due to the beating of different local modes $\vec{T}_{2j}$ inside the polymer core [18].

An analysis of a sensor for temperature measurements in accordance with the present invention will now be described. As previously stated the polymer core serves as a FPI cavity, i.e. it introduces two reflective interfaces; one at the SMF/polymer interface and the other at the polymer/air interface. The light traveling in the fiber core is first partially reflected at the fiber/polymer interface due to the difference between the refractive indices of the optical fiber and the polymer. The transmitted light then travels inside the polymer core and again is partially reflected at the polymer/air interface. When these two reflected lights are recombined in the optical fiber, they interfere with each other due to the different optical paths they have traveled. The interference spectrum contributed by the light reflected at the SMF/polymer interface $I_1$ and the light reflected at the polymer/air interface $I_2$ can be expressed as:

$$I = I_1 + I_2 + 2\sqrt{I_1 I_2} \cos(\phi_{12}). \quad (9)$$

The phase shift $\phi_{12}$ is determined by the optical path difference (OPD) traveled by $I_1$ and $I_2$. Because the polymer tip does not have a cladding region, it operates as a multi-mode fiber ($n_{core}=1.54$, $n_{clad}=1.0$, V=23 at 1310 nm) with multiple higher-order modes propagating inside it. When these higher-order modes reenter the optical fiber, they are partially coupled back to the fundamental mode due to the mode-coupling effect of the SMF/polymer interface. As a result, the interference spectrum is a summation of the interferences between the fundamental mode reflected at the SMF/polymer interface and the fundamental mode converted from the higher order modes propagating in the polymer tip [20], i.e.:

$$I_{12}(\lambda) = \sum_j \left[ I_1 + I_{12,j} + 2\sqrt{I_1 I_{12,j}} \cos(\phi_{12,j}) \right], \quad (10)$$

where $I_{12,j}$ is the intensity of the light converted from the $j^{th}$ mode to the fundamental mode and $\phi_{12,j}$ is the phase shift between the fundamental mode $I_1$ traveling in the fiber and the $j^{th}$-order mode $I_{2,j}$ traveling in the polymer tip. For the fundamental mode $I_{2,1}$, the phase shift $\phi_{12,1}$ can be expressed as:

$$\phi_{12,1} = 2\beta_1 L, \quad (11)$$

where L is the physical length of the polymer core. The propagation constant of the fundamental mode $\beta_1$ can be calculated from the wavelength $\lambda$, the refractive index of the polymer core $n_{core}$, the V number V, and the polymer core radius $\rho$ [21], i.e.:

$$\beta_1 = \frac{2\pi n_{core}}{\lambda}\left[1 - \left(\frac{U_{1\infty}e^{(-1/V)}\lambda}{2\pi \rho n_{core}}\right)^2\right]^{1/2}, \quad (12)$$

where the modal parameter of the $LP_{0j}$ mode, $U_{j\infty}$, is given by the root of the Bessel function of zero order, i.e.:

$$J_0(U_{j\infty}) = 0. \quad (13)$$

For the higher order modes, the phase shift $\phi_{12,j}$ can be calculated as [21]:

$$\phi_{12,j} = 2(\beta_1 + \Delta\beta_{1j})L, \quad (14)$$

where $\Delta\beta_{1j}$ is the difference between the propagation constants of the fundamental mode $LP_{01}$ and the $j^{th}$ order mode $LP_{0j}$. At a large V number, $\Delta\beta_{1j}$ can be approximated as [22]:

$$\Delta\beta_{1j} = \frac{(U_{j\infty}^2 - 2.404^2)\lambda}{4\pi\rho^2 n_{core}}\exp(-2/V), \quad (15)$$

Since $\Delta\beta_{1j}$ is much smaller than $\beta_1$ for large V numbers, it only introduces a small phase shift to the interference spectrum $I_{12}$. Therefore, the OPD of the two interfering lights is mainly determined by $2\beta_1 L$. Combining Eq. (3) and (4), we can express the OPD as:

$$OPD = \frac{\phi_{12}}{2\pi\chi} = 2n_{core}L\left[1 - \left(\frac{U_{1\infty}e^{(-1/V)}\lambda}{2\pi\rho_{ncore}}\right)^2\right]^{1/2} \approx 2n_{core}L, \quad (16)$$

where $\chi$ is the wave number. Equation (8) indicates that the OPD is a function of the refractive index and the length of the polymer core. Since temperature affects these two parameters, a change in the ambient air temperature will cause a change in the OPD, and thus results in a shift in the reflectance spectrum.

The effect of temperature change on the OPD can be found by differentiating equation (16) with respect to temperature, i.e.:

$$\frac{d(OPD)}{dT} = 2\left(\frac{dn_{core}}{dT}L + n_{core}\frac{dL}{dT}\right) \quad (17)$$

$$= 2n_{core}L\left(\frac{1}{n_{core}}\frac{dn_{core}}{dT} + \frac{1}{L}\frac{dL}{dT}\right).$$

Expressing the thermal expansion coefficient and thermo-optic coefficient of the polymer core material as $$\alpha = \frac{1}{L}\frac{dL}{dT} \text{ and } \xi = \frac{1}{n_{core}}\frac{dn_{core}}{dT},$$

we can establish the relationship between the OPD changes and the temperature variations as:

$$\frac{\Delta(OPD)}{OPD} = (\alpha + \xi)\Delta T. \quad (18)$$

As a result, the temperature variation is defined by:

$$\Delta T = \frac{\Delta(OPD)}{OPD(\alpha + \xi)} \quad (19)$$

Figure 9:
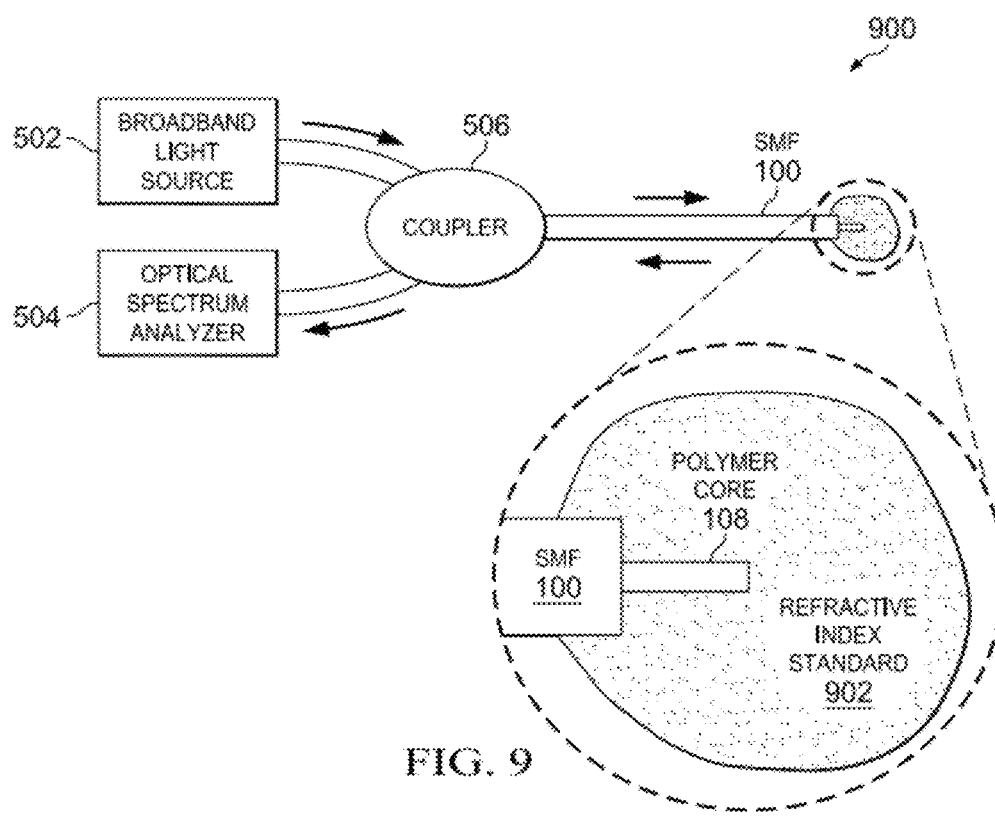
FIG. 9 shows a sensor setup for measuring RI in accordance with one embodiment of the present invention.

Now referring to FIG. 9, the study setup 900 to evaluate the RI sensor 100 using the white light reflectance measurement system in accordance with the present invention is shown. The optical fiber RI sensor 100 is bonded to a microscope slide and a drop of liquid standard 902 with known RI (Cargille, #18065 series AA) was dropped on the polymer core 108. Because of surface tension, the liquid 902 forms a thick film around the polymer core 108 and thus to change its external RI. After the measurement, the RI sensor 100 was rinsed with alcohol to clear out the residual RI liquid 108 before the next experiment. The reflectance spectrum of the sensor 100 after cleaning was also checked to make sure that the RI liquid 902 did not permanently change the characteristics of the polymer core 108.

Figure 10A:
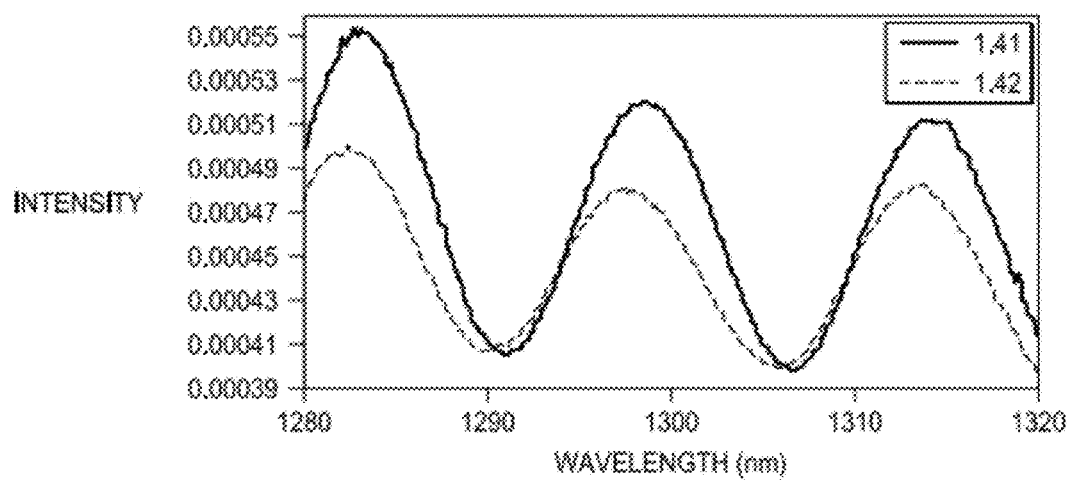
FIGS. 10A-10C show the shift of the interference fringes with external RI: shift of reflectance spectra (FIG. 10A), study results using RI standards (FIG. 10B), simulation results assuming $C_{1j}=C_{j1}=[0.5, 0.3, 0.12, 0.08]$ (FIG. 10C) in accordance with the present invention.
Figure 10B:
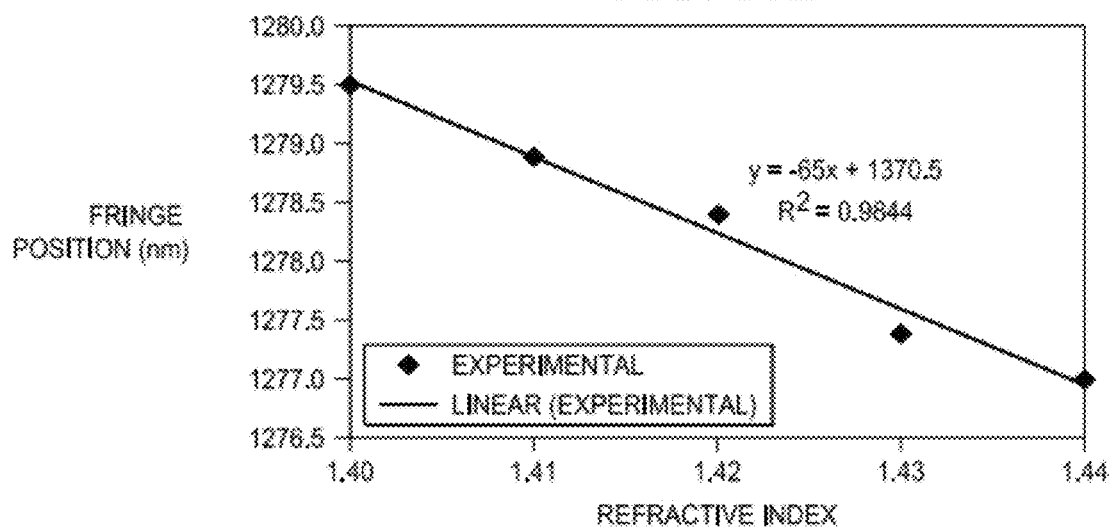

The reflectance spectra of the sensor 100 with two different external RIs are shown in FIG. 10A. Changing the RI from 1.41 to 1.42 not only shifted the fringes to the left but also reduced the fringe visibility. This is because an increase in the external RI also reduces the intensity of the light reflected at the polymer/air interface. The performance of the fabricated sensor for RI measurement was characterized by submerging it in five RI standards with RI ranging from 1.40 to 1.44. The reflectance spectrum of the RI sensor was first low-pass filtered to remove high frequency noises before determining the fringe locations. The fringe positions at different external RIs are shown in FIG. 10B. Based on the linear fitting of the experimental data, a change of RI by 0.01 caused a shift of 0.65 nm in the fringe positions. Assuming the measurement system has a spectral resolution of 1 pm [3, 5, 6], the RI resolution of the sensor is estimated to be 1.5e-5.

Figure 10C:
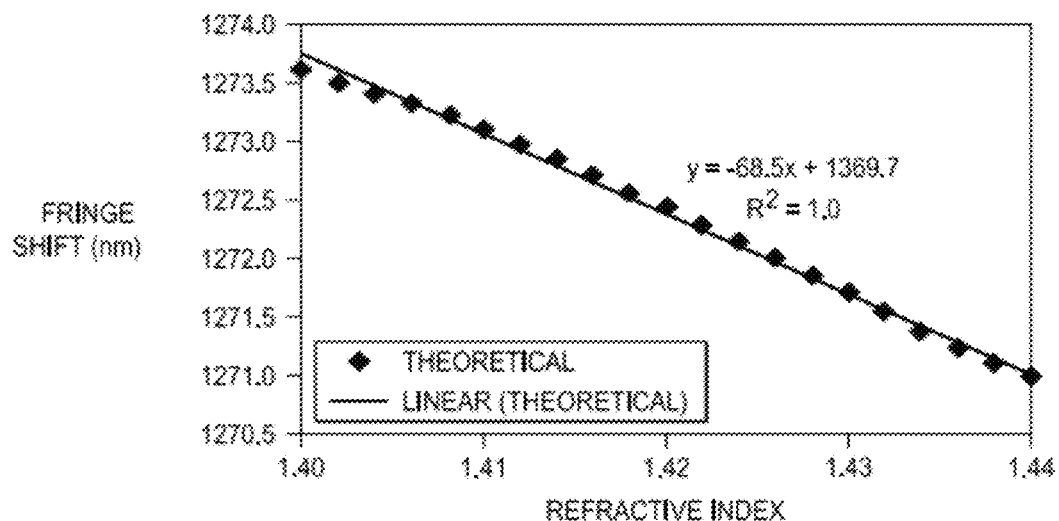

The mode coupling at the SMF/polymer interface has a strong influence on the sensitivity of the RI sensor. Based on the calculation of $\beta_j$, the higher order modes are more sensitive to the RI changes. To achieve the RI sensitivity observed by the experiment, we estimated at least four local modes should be presented in the polymer core with the power transfer coefficients $C_{1j}=C_{j1}=[0.5, 0.3, 0.12, 0.08]$ (see FIG. 10C). The exact values of $C_{1j}$ and $C_{j1}$ are determined by the wavelength used, the geometry and RI of the polymer core, and the external RI.

Figure 11:
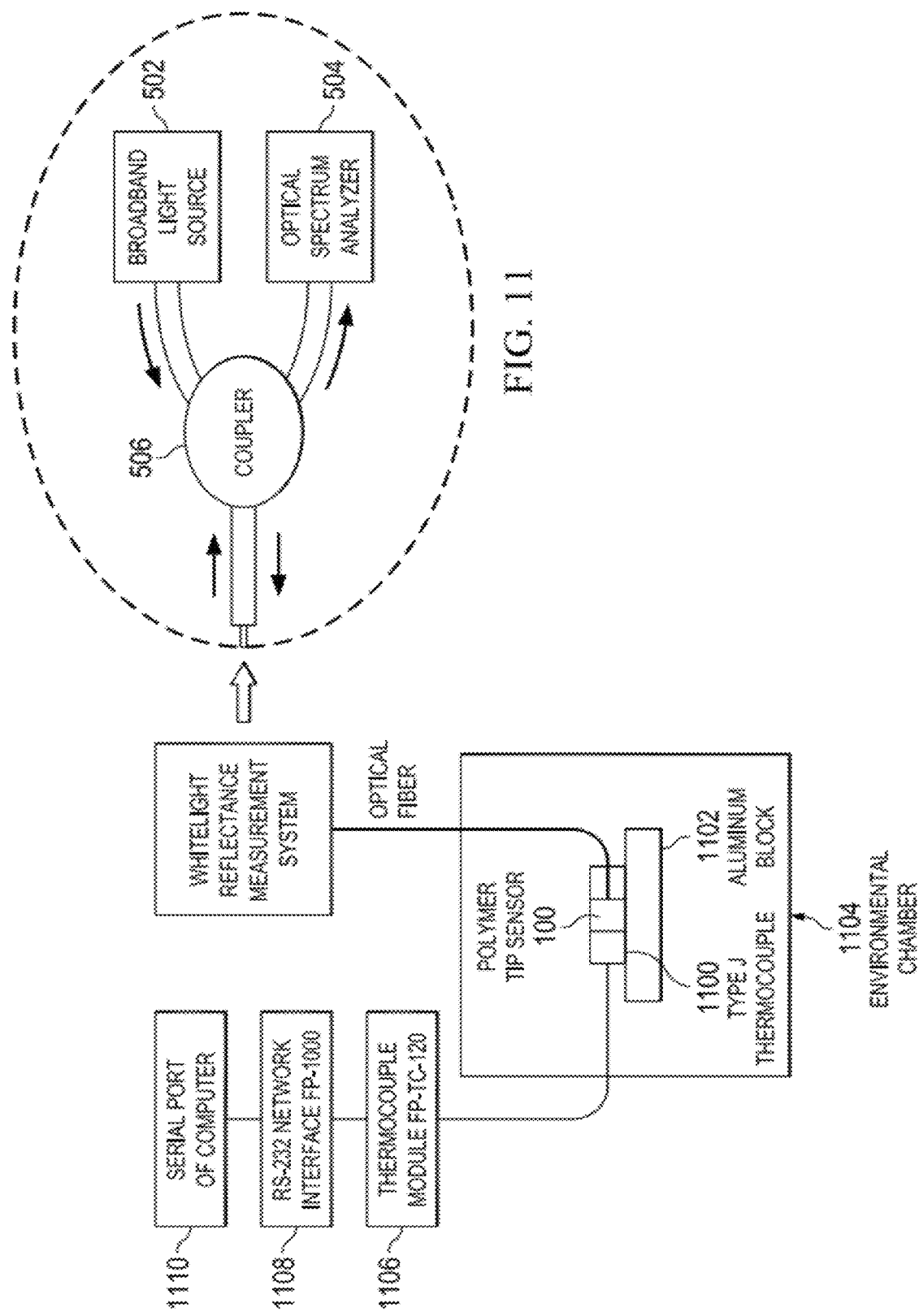
FIG. 11 shows a set up for the polymer core-based temperature sensor evaluation according to an embodiment of the present invention.

Referring now to FIG. 11, the performance of the polymer core-based temperature sensor 100 in accordance with the present invention was evaluated from room temperature to 49° C. The polymer core sensor 100 as well as a type J thermocouple 1100 (SA1-J, Omega Engineering) were bonded to an aluminum block 1102 and were placed in an environmental chamber 1104 (Quincy Lab, Model 30 GC). The thermocouple 1100 was connected to an 8-Channel thermocouple signal conditioning module 1106 (National Instruments FP-TC-120) with built in zero point compensation, which was connected to a computer 1110 through a RS-232 network interface 1108 (National Instruments, FP-1000). The temperature inside the oven was adjusted from 27° C. to 49°

C. with the increment of around 4° C. At every temperature setting, there was a half an hour waiting period in order for the thermocouple reading to reach a steady state value. A LabVIEW program was developed to trace the reflectance spectrum of the sensor automatically after the thermocouple reading is stabilized.

The whitelight reflectance spectrum measurement system shown in FIG. 5 was again used to record the fringe spectrum of the polymer core sensor. A MATLAB program was developed to filter and normalize the reflectance signal. The fringe spectrum of the sensor was first converted from wavelength scale to wave number scale. After filtering the reflectance spectrum using a low pass filter to remove the high frequency noise, the filtered signal was normalized with the spectrum of the light source. Subsequently, the OPD of the sensor was demodulated using a linear fitting algorithm described by Schwider and Zhou [27].

Figure 12:
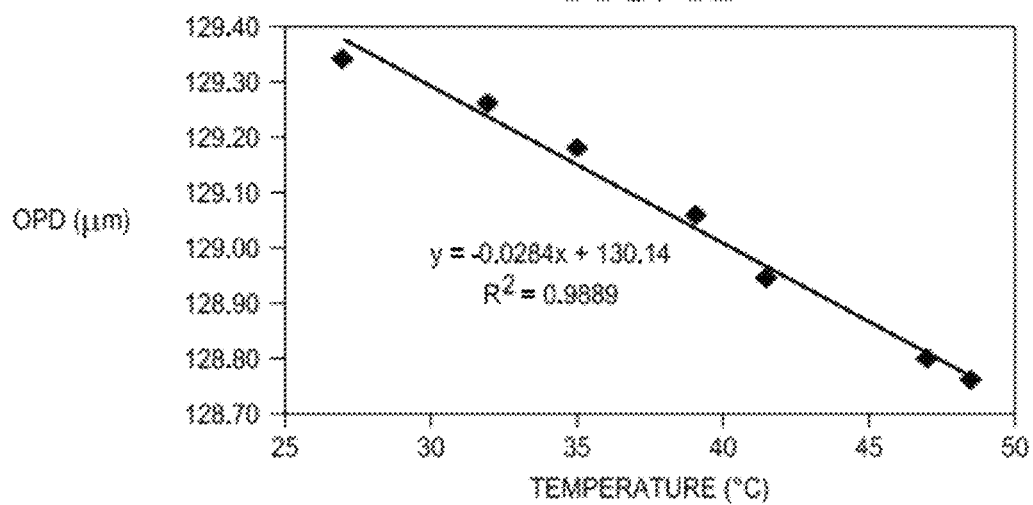
FIG. 12 shows the OPD change of the temperature sensor between 27-49° C. in accordance with the present invention.

The performance of the sensor is evaluated with a 42 μm long polymer core using a central wavelength of 1310 nm. The results can be summarized with the graph shown in FIG. 12. The temperature sensitivity of the sensor is described in terms of the OPD change per Celsius degree of change in temperature [28]. Study results showed that OPD sensitivity of the sensor is −28.4 nm/° C. The OPD sensitivity is negative because the polymer has a negative thermo-optic coefficient. This indicates that the thermo-optic effect of the polymer material is more dominant than the thermal expansion effect. Based on the thermal expansion coefficient of the NOA68 provided by the manufacturer ($\alpha=2.1*10^{-4}$ 1/° C.) and the measured OPD sensitivity, we calculated that the polymer material should have a thermo-optic coefficient of $-4.3*10^{-4}$ 1/° C. This value is about three times larger than the value predicted by an empirical relationship presented in [29]. The discrepancy is due to the fact that the empirical relationship was obtained at a wavelength of 1550 nm while the wavelength used by the inventors in the study was 1310 nm and the chemical structure of the polymer. Considering that polymer materials have very diverse material properties, the estimated thermo-optical coefficient is comparable with the expected value.

Figure 13A:
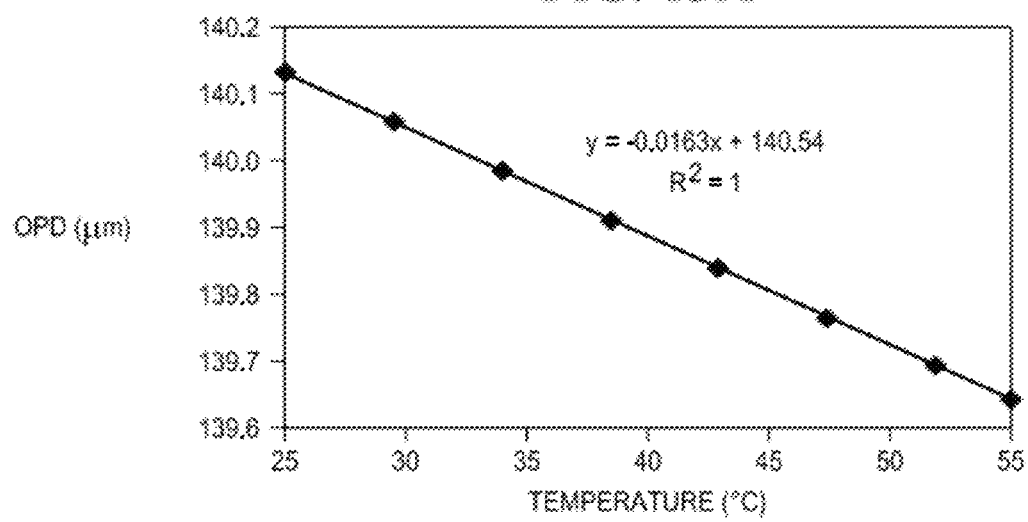
FIGS. 13A-13B show the OPD change of the temperature sensor between 25-55° C. and 68-100° C. in accordance with the present invention.
Figure 13B:
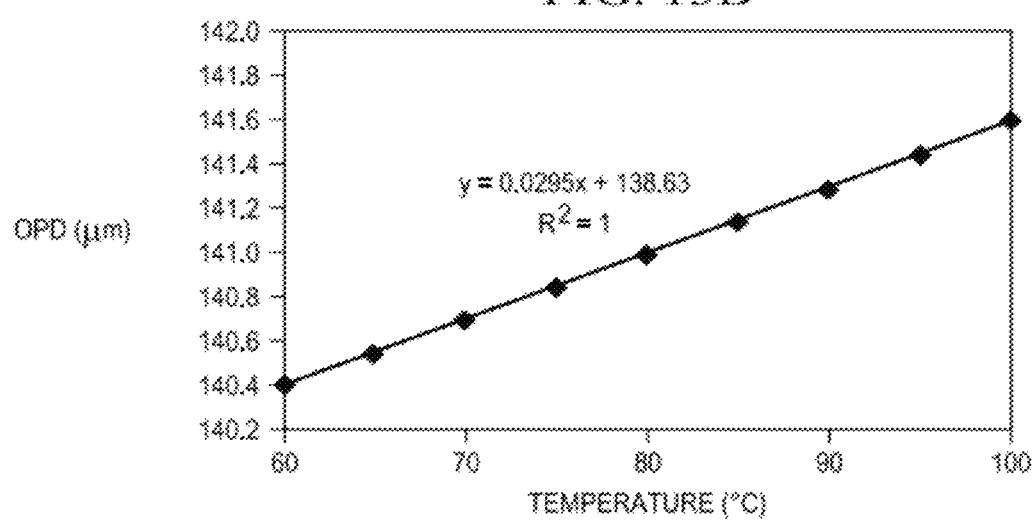

Now referring to FIGS. 13A-13B, the OPD change of the temperature sensor between 25-55° C. and 68-100° C. is shown in accordance with the present invention. For the simulation and actual measurements for the graphs shown in FIG. 13A-13B, the sensor had the following characteristics:

|   | Temperature Range | |
|---|---|---|
|   | 25-55° C. | 68-100° C. |
| L | 45 μm | 45 μm |
| n | 1.5605 @ 25° C. | 1.555 @ 68-100° C. |
| β | $-3.3*10^{-4}$ 1/C | 0 |
| α | $2.1*10^{-4}$ 1/C | $2.1*10^{-4}$ 1/C |

The measured sensitivity versus the theoretical sensitivity was:

| Temperature ° C. | Measured Sensitivity (nm/° C.) | Theoretical Sensitivity (nm/° C.) |
|---|---|---|
| 25-55 | −14.9 | −16.3 |
| 68-100 | 31.5 | 29.5 |

When the present invention is used for distance measurement, there is no limit on the minimum measurement distance. Note that the minimum distance actually measured was 4 microns. The fringe spacing is directly related to the OPD:

$$d = \frac{\lambda_1 \lambda_2}{2n_0(\lambda_2 - \lambda_1)} - \Delta nL. \tag{20}$$

Figure 14:
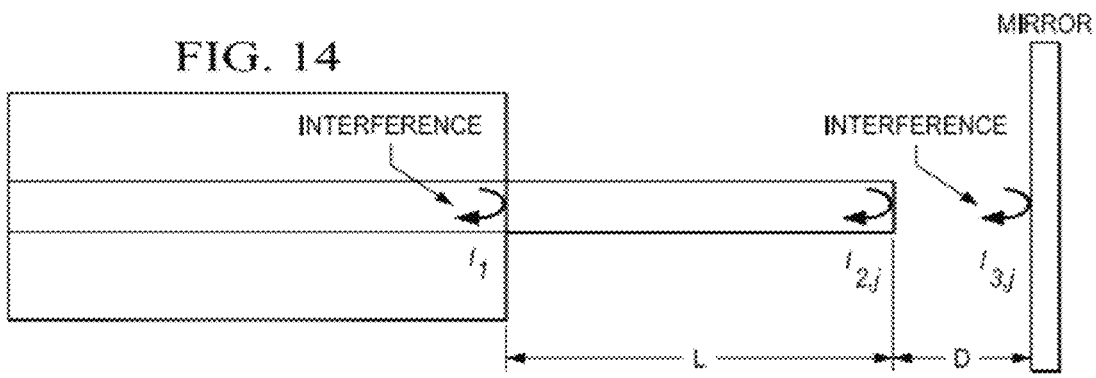
FIG. 14 shows a diagram for using a sensor to measure distance in accordance with the present invention.

FIG. 14 shows a diagram for using a sensor 100 to measure distance in accordance with the present invention:

$$I(\lambda) = \sum_j \left| I_1 + I_{3,j} + 2\sqrt{I_1 I_{3,j}} \cos(\phi_j) \right| \tag{21}$$

where $$\phi_j = 2\left(\beta_1 L + \Delta\beta_{1j} L + \frac{2\pi n_m d}{\lambda}\right). \tag{22}$$

Figure 15:
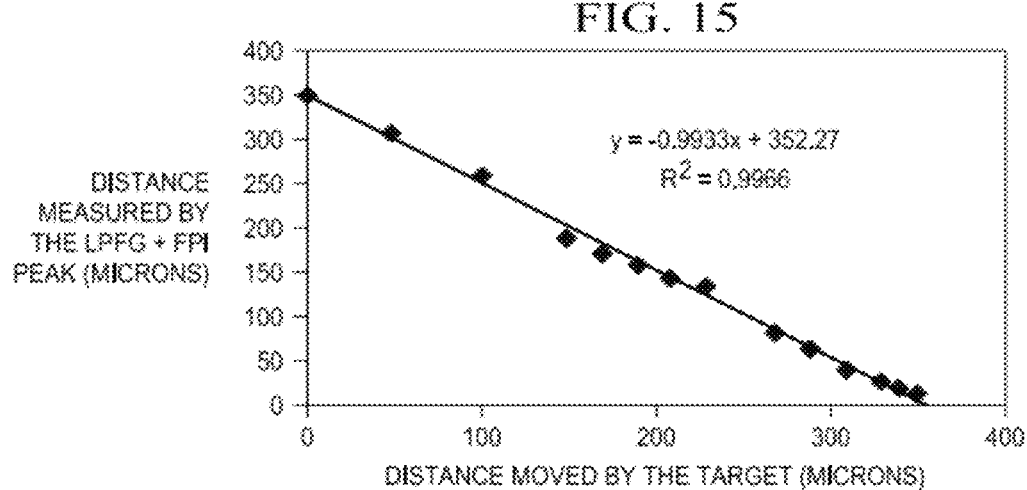
FIG. 15 shows a graph of the actual distance moved by the target and the actual distance calculated using a sensor in accordance with the present invention.

FIG. 15 shows a graph of the actual distance moved by the target and the actual distance calculated using a sensor in accordance with the present invention.

Figure 17:
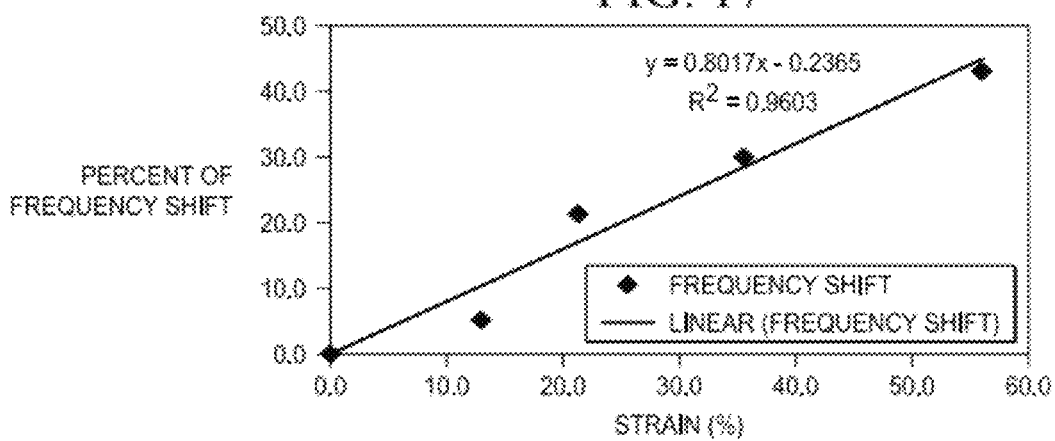
FIG. 17 is a graph showing the strain measurements in accordance with one embodiment of the present invention.
Figure 16A:
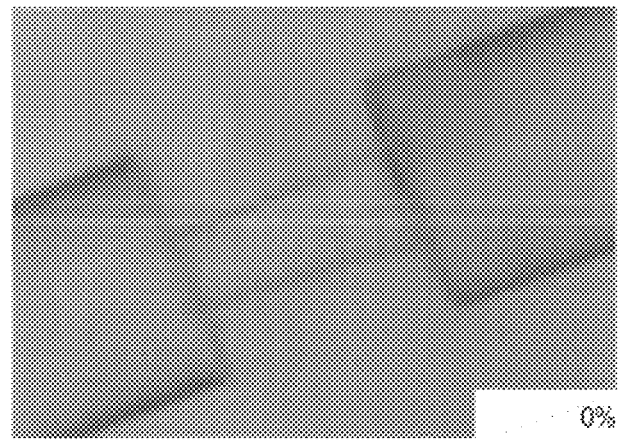
FIGS. 16A-F are micrographic images illustrating the use of the present invention as a strain sensor.
Figure 16B:
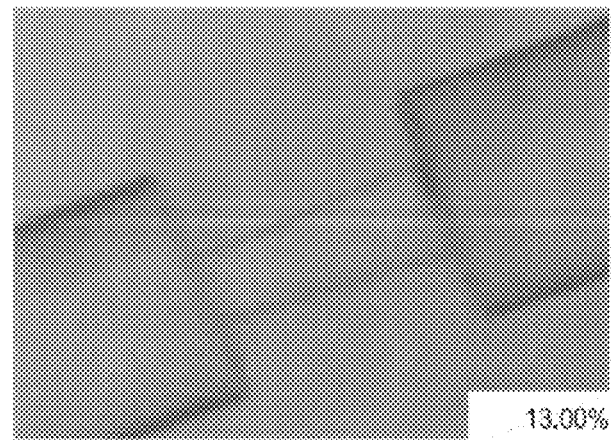
Figure 16C:
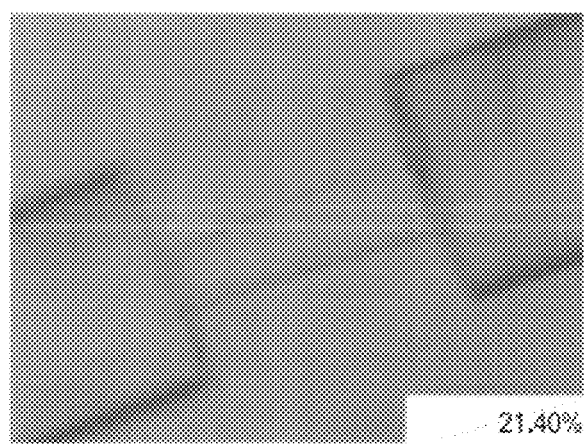
Figure 16D:
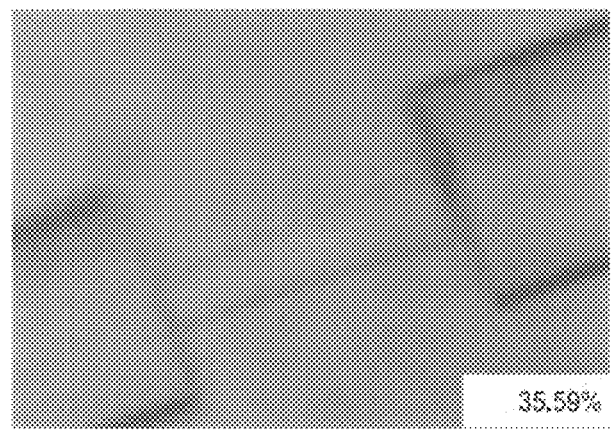
Figure 16E:
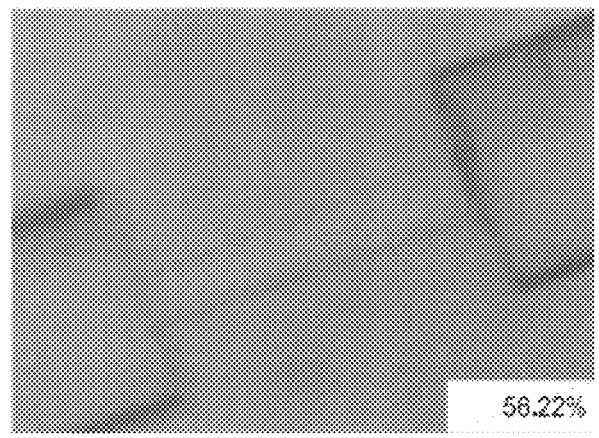
Figure 16F:
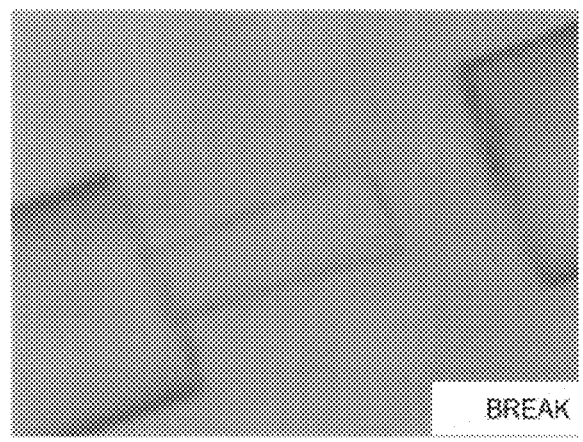

An example of using the present invention as a strain sensor is shown in FIGS. 16A-F. A graph showing the measurements is shown in FIG. 17.

Figure 18A:
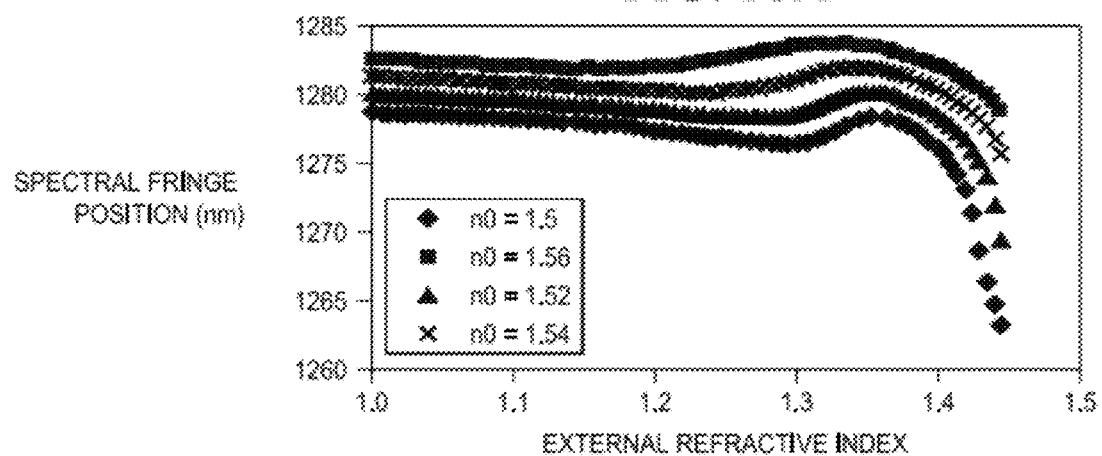
FIGS. 18A-18B show graphs of the sensor response to external refractive index in accordance with the present invention.
Figure 18B:
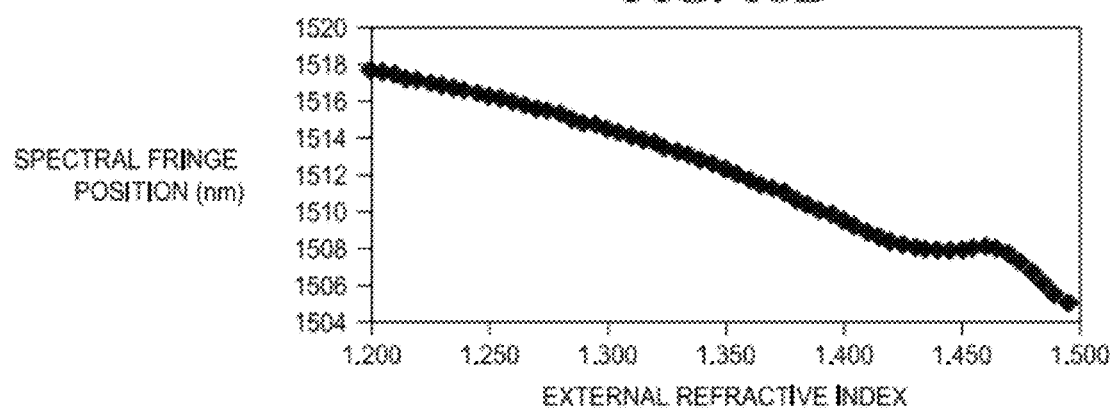

The sensor provided by the present invention can be designed for the range/sensitivity required. FIG. 18A-18B show graphs of the sensor response to external refractive index.

In summary, the present invention describes a low cost fabrication technique to produce a compact optical fiber RI and temperature sensor. The sensitivity of the sensor to external RI changes was evaluated using RI standards. The RI resolution of the sensor is estimated to be 1.5e-5, assuming the measurement system has a spectral resolution of 1 pm. The design of the RI sensor, such as the RI and the length of the polymer core, can be easily adjusted using the fabrication technique of the present invention. The polymer tip sensor of the present invention was also evaluated for temperature measurements. Due to the high thermo-optic coefficient of the polymer material, a highly sensitive sensor was demonstrated. The sensitivity of the sensor can be further improved by tailoring the length of polymer tip or using a different polymer material.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

REFERENCES

1. T. Allsop, R. Reeves, D. J. Webb, I. Bennion, R. Neal, "A high sensitivity refractometer based upon a long period grating Mach-Zehnder interferometer", Rev. Sci. Instrum., 73, 4, 1702-1705 (2002).
2. H. J. Patrick, A. D. Kersey, and F. Bucholtz, "Analysis of the response of long period fiber gratings to external index of refraction", J. Lightwave Tech., 16, 9, 1606-1612 (1998).
3. A. Iadicicco, A. Cusano, S. Campopiano, A. Cutolo, and M. Giordano, "Thinned fiber bragg gratings as refractive index sensors", IEEE Sens. J., 5, 6, 1288-1295 (2005).
4. A. Iadicicco, S. Campopiano, A. Cutolo, M. Giordano, and A. Cusano, "Refractive Index Sensor based on microstructured fiber bragg grating", IEEE Phot. Tech. Lett., 17, 6, 1250-1252 (2005).
5. K. Schroeder, W. Ecke, R. Mueller, R. Willsch and A. Andreev, "A fiber Bragg grating refractometer", Meas. Sci. Technol., 12, 757-764 (2001).
6. M. C. Phan Huy, G. Laffont, Y. Frignac, V. Dewynter-Marty, P. Ferdinand, P. Roy, J-M Blondy, D. Pagnoux, W. Blanc and B. Dussardier, "Fibre Bragg grating photowriting in microstructured optical fibers for refractive index measurement", 17, 992-997 (2006).
7. Z. Tian, S. S-H Yam, and H. Loock, "Refractive index sensor based on abrupt taper Michelson interferometer in a single-mode fiber", Opt. Lett., 33, 10, 1105-1107 (2008).
8. J. Ding, A. P. Zhang, L. Y. Shao, J. H. Yan, and S. He, "Fiber-taper seeded long-period grating pair as a highly sensitive refractive-index sensor", IEEE Phot. Tech. Lett., 17, 6, 1247-1249 (2005).
9. B. Culshaw, F. Muhammad, and G. Stewart, "Evanescent wave methane detection using optical fibers", Electron. Lett., 28, 24, 2232-2234 (1992).
10. F. M. Cox, R. Lwin, M. C. J. Large, and C. M. B Cordeiro, "Opening up optical fibres", Opt. Exp., 15, 19, 11843-18848 (2007).
11. K. Newby, W. M. Reichart, J. D. Andrade, and R. E. Benner, "Remote spectroscopic sensing of chemical absorption using a single multimode optical fiber", App. Opt., 23, 11, 1812-1815 (1984.)
12. R. Hypszer, "Fibre optic temperature sensors", *Proceedings of SPIE*, Vol. 2634, 1999, pp. 34-46.
13. X. Chen, F. Shen, A. Wang, Z. Wang and Y. Zhang, "Novel Fabry-Perot fiber optic sensor with multiple applications", *Proceedings of SPIE*, Vol. 5590, 2004, pp. 111-121.
14. C. E. Lee, H. F. Taylor, A. M. Markus and E. Udd, "Optical fiber Fabry-Perot embedded sensor", *Optics Letters*, Vol. 14, 1989, pp. 1225-1227.
15. H. Singh and J. S. Sirkis, "Simultaneously measuring temperature and strain using optical fiber microcavities", *Journal of Lightwave Technology*, Vol. 15, No. 4, 1997, pp. 647-653.
16. W. H. Tsai and C. J. Lin, "Novel structure for the intrinsic Fabry-Perot fiber optic temperature sensor", *Journal of Lightwave Technology*, Vol. 19, 2001, pp 682-686.
17. Z. Huang, Y. Zhu, X. Chen, and A. Wang, "Intrinsic Fabry-Perot fiber sensor for temperature and strain measurements", IEEE Phot. Tech. Lett., 17, 11, 2403-2405 (2005).
18. Lacroix, R. Bourbonnais, F. Gonthier, and J. Bures, "Tapered monomode optical fibers: understanding large power transfer", App. Opt., 25, 23, 4421-4425 (1986).
19. R. J. Black, S. Lacroix, F. Gonthier, and J. D. Love, "Tapered single-mode fibers and devices Part 2: Experimental and theoretical quantification", IEE Proc. J, 138, 5, 355-364 (1991).
20. S. Lacroix, et al., "Tapered monomode optical fibers: understanding large power transfer", *Applied Optics*, Vol. 25, 1986, pp. 4421-4425.
21. A. W. Snyder, "Coupling of modes on a tapered dielectric cylinder", *IEEE Transactions on Microwave Theory and Techniques*, Vol. 18, 1970, pp. 383-392.
22. D. T. Cassidy, D. C. Johnson and K. O. Hill, "Wavelength-dependent transmission of monomode optical fiber tapers", *Applied Optics*, Vol. 24, 1985, pp. 945-950.
23. S. J. Frisken, "Light-Induced optical waveguide uptapers", Opt. Lett. 18, 1035-1037 (1993).
24. O. Sugihara, H. Tsuchie, H. Endo, N. Okamoto, T. Yamashita, M. Kagami, and T. Kaino, "Light-Induced self-written polymeric optical waveguides for single-mode propagation and for optical interconnections", IEEE Phot. Tech. Lett. 16, 804-806 (2004).
25. A. Majumdar, and H. Huang, "Development of an in-fiber whitelight interferometric distance sensor for absolute measurement of arbitrary small distances", Applied Optics, 47, 15, 2821-2828 (2008).
26. M. Hocine, N. Fressengeas, G. Kugel, C. Carré, D. J. Lougnot, R. Bachelot, and P. Royer, "Modeling the growth of a polymer microtip on an optical fiber end", *J. Opt. Soc. Am. B*, 23, 4, 611-620 (2006).
27. J. Schwider and L. Zhou, "Dispersive interferometric profilometer", *Optics Letters*, Vol. 19, 1994, pp. 995-997.
28. D. W. Kim, F. Shen, X. Chen and A. Wang, "Simultaneous measurement of refractive index and temperature based on a reflection-mode long-period grating and an intrinsic Fabry-Perot interferometer sensor", *Optics Letters*, Vol. 30, 2005, pp. 3000-3002.
29. Z. Zhang, P. Zhao, P. Lin and F. Sun, "Thermo-optic coefficients of polymers for optical waveguide applications", *Polymer*, Vol. 47, 2006, pp. 4983-4986.

What is claimed is:

1. A method for fabricating an optical fiber based polymer core sensor comprising the steps of:
providing an optical fiber having a core;
aligning a flat reflective object with the core of the optical fiber to provide a gap between the core and the flat reflective object;
depositing a light-curable polymer within the gap;
transmitting a light through the core such that the light-curable polymer forms a cured polymer core connecting the core to the reflective object, wherein the cured polymer core has a diameter approximately equal to the core; and
removing the reflective object such that the cured polymer core remains affixed to the optical fiber.

2. The method as recited in claim 1, further comprising the steps, prior to depositing the light-curable polymer, of:
transmitting a white light through the optical fiber;
measuring the gap using the optical fiber and the reflective object as a white light Fabry-Perot interferometric distance sensor; and
adjusting the gap to provide a specified distance between the optical fiber and the reflective object.

3. The method as recited in claim 1, further comprising the steps of:
removing any uncured light-curable polymer; and
packaging the cured polymer core and a portion of the first optical fiber.

4. The method as recited in claim 3, wherein the cured polymer core and the optical fiber are packaged within a capillary tube.

5. The method as recited in claim 1, further comprising the step of modifying a shape of the cured polymer core.

6. The method as recited in claim 5, wherein:
the shape of the cured polymer core is substantially cylindrical; and
the modified shape of the cured polymer core is tapered or geometrically shaped.

7. The method as recited in claim 1, further comprising the step of controlling a length of the cured polymer core by measuring and adjusting the gap between the optical fiber and the reflective object.

8. The method as recited in claim 1, wherein:
the flat reflective object comprises a second optical fiber or a mirror; or
the light-curable polymer comprises a UV-curable polymer and the light comprises a UV light.

9. The method as recited in claim 1, wherein:
the light is generated using a light-emitting-diode (LED) or other light source attached to the optical fiber that is suitable for curing the light-curable polymer; and
the light-curable polymer comprises a light-curable optical epoxy.

10. The method as recited in claim 1, wherein the light-curable polymer is selected or modified to adjust a sensitivity or a range of the refractive index sensor.

11. The method as recited in claim 1, wherein the cured polymer core has a higher reflective index than the light-curable polymer and acts as a waveguide to confine the light inside the cured polymer core.

12. The method as recited in claim 1, wherein a refractive index of the optical fiber is different that a refractive index of the cured polymer core.

13. The method as recited in claim 1, wherein the cured polymer core serves as a Fabry-Perot cavity that introduces a phase shift to a light propagating through the cured polymer core from the first optical fiber.

14. The method as recited in claim 1, wherein the optical fiber based polymer core sensor has a reflectance spectrum of $$I(\lambda) = I_1^{(r)} + \sum_j I_1^{(2j)} + \sum_j \sqrt{I_1^{(r)} I_1^{(2j)}} \cos(2\beta_j L) + \sum_{i \neq j} \sqrt{I_1^{(2i)} I_1^{(2j)}} \cos[2(\beta_j - \beta_i)L].$$

15. The method as recited in claim 1, wherein the optical fiber based polymer core sensor is used to measure a temperature, measure a strain, measure a distance, measure a refractive index, detect or measure an analyte, detect a toxin, detect a biological agent, monitor a chemical process, or a combination thereof.

16. The method as recited in claim 1, wherein the optical fiber based polymer core sensor is used to measure a temperature change as defined by $$\Delta T = \frac{\Delta(OPD)}{OPD(\alpha + \xi)}.$$

17. A method for fabricating an optical fiber based polymer core sensor comprising the steps of:
providing an optical fiber having a core;
aligning a flat reflective object with the core of the optical fiber to provide a gap between the core and the flat reflective object;
transmitting a white light through the optical fiber;
measuring the gap using the optical fiber and the reflective object as a white light Fabry-Perot interferometric distance sensor;
adjusting the gap to provide a specified distance between the optical fiber and the reflective object;
depositing a light-curable polymer within the gap;
transmitting a light through the core such that the light-curable polymer forms a cured polymer core connecting the core to the reflective object, wherein the cured polymer core has a diameter approximately equal to the core;
removing the reflective object such that the cured polymer core remains affixed to the optical fiber;
removing any uncured light-curable polymer; and
packaging the cured polymer core and a portion of the first optical fiber.

18. An optical fiber based polymer core sensor comprising:
an optical fiber having a core and an end; and
a cured polymer core affixed to the core of the optical fiber and extending outward from the end of the optical fiber wherein the cured polymer core has a diameter approximately equal to the core of the optical fiber, wherein the cured polymer core is fabricated in accordance with the method of claim 1.

19. The optical fiber based polymer core sensor as recited in claim 18, wherein the cured polymer core and a portion of the optical fiber are disposed within a package.

20. The optical fiber based polymer core sensor as recited in claim 18, wherein the cured polymer core is substantially cylindrical, tapered or geometrically shaped.

21. The optical fiber based polymer core sensor as recited in claim 18, wherein the light-curable polymer is selected or modified to adjust a sensitivity or a range of the optical fiber based polymer core sensor.

22. The optical fiber based polymer core sensor as recited in claim 18, wherein a refractive index of the optical fiber is different that a refractive index of the cured polymer core.

23. The optical fiber based polymer core sensor as recited in claim 18, wherein the cured polymer core serves as a Fabry-Perot cavity that introduces a phase shift to a light propagating through the cured polymer core from the optical fiber.

24. The optical fiber based polymer core sensor as recited in claim 18, wherein the optical fiber based polymer core sensor has a reflectance spectrum of $$I(\lambda) = I_1^{(r)} + \sum_j I_1^{(2,j)} + \sum_j \sqrt{I_1^{(r)} I_1^{(2,j)}} \cos(2\beta_j L) + \sum_{i \neq j} \sqrt{I_1^{(2i)} I_1^{(2,j)}} \cos[2(\beta_j - \beta_i)L].$$

25. The optical fiber based polymer core sensor as recited in claim 18, wherein the refractive index sensor is used to measure a temperature, measure a strain, measure a distance, measure a refractive index, detect or measure an analyte, detect a toxin, detect a biological agent, monitor a chemical process, or a combination thereof.

26. The optical fiber based polymer core sensor as recited in claim 18, wherein the optical fiber based polymer core sensor is used to measure a temperature change as defined by $$\Delta T = \frac{\Delta(OPD)}{OPD(\alpha + \xi)}.$$

* * * * *